(12) United States Patent
Tsuji et al.

(10) Patent No.: US 12,038,488 B2
(45) Date of Patent: Jul. 16, 2024

(54) MEASURING APPARATUS, MEASURING METHOD AND RECORDING MEDIUM

(71) Applicant: ASAHI KASEI KABUSHIKI KAISHA, Tokyo (JP)

(72) Inventors: Hideyuki Tsuji, Tokyo (JP); Shigeki Okatake, Tokyo (JP); Masashi Yamada, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 186 days.

(21) Appl. No.: 17/454,623

(22) Filed: Nov. 12, 2021

(65) Prior Publication Data

US 2022/0065953 A1 Mar. 3, 2022

Related U.S. Application Data

(63) Continuation of application No. PCT/JP2020/020202, filed on May 21, 2020.

(30) Foreign Application Priority Data

May 31, 2019 (JP) ................................. 2019-103194

(51) Int. Cl.
*G01R 33/02* (2006.01)
*A61B 5/0536* (2021.01)
(Continued)

(52) U.S. Cl.
CPC ........ *G01R 33/0206* (2013.01); *A61B 5/0536* (2013.01); *G01R 33/0017* (2013.01); *G01R 33/0094* (2013.01); *G01R 33/091* (2013.01)

(58) Field of Classification Search
CPC ............... G01R 33/00; G01R 33/0017; G01R 33/0094; G01R 33/02; G01R 33/0206;
(Continued)

(56) References Cited

U.S. PATENT DOCUMENTS

| 5,421,345 A | 6/1995 | Lekholm |
| 6,263,230 B1 | 7/2001 | Haynor |

(Continued)

FOREIGN PATENT DOCUMENTS

| CN | 102499682 A | 6/2012 |
| CN | 207912687 U | 9/2018 |

(Continued)

OTHER PUBLICATIONS (ISA/237) Written Opinion of the International Search Authority for International Patent Application No. PCT/JP2020/020202, issued/mailed by the Japan Patent Office on Aug. 4, 2020.

(Continued)

*Primary Examiner* — Hoai-An D. Nguyen

(57) ABSTRACT

A measurement in a high accuracy is performed when acquiring a tomographic image or the like. Provided is a measuring apparatus, including an electrode unit including a plurality of electrodes in contact with a living body; a magnetic sensor array, including a plurality of magnetic sensor cells, capable of detecting input magnetic fields in three axial directions in a plurality of positions in a three-dimensional space; a current applying section configured to apply a current flowing in the living body by at least one electrode pair of the plurality of electrodes; a measurement data acquiring section configured to acquire measurement data based on the input magnetic field. Which is detected from the living body by the magnetic sensor array during a current flows in the living body; and an estimation section configured to estimate a current flowing in the living body based on the measurement data.

19 Claims, 17 Drawing Sheets

(51) Int. Cl.
*G01R 33/00* (2006.01)
*G01R 33/09* (2006.01)

(58) Field of Classification Search
CPC ...... G01R 33/06; G01R 33/09; G01R 33/091; A61B 5/00; A61B 5/05; A61B 5/053; A61B 5/0536
USPC .................................................. 324/200, 260
See application file for complete search history.

(56) References Cited

U.S. PATENT DOCUMENTS

| | | |
|---|---|---|
| 2007/0108962 A1 | 5/2007 | Taulu |
| 2008/0211492 A1 | 9/2008 | Tsukada |
| 2011/0081058 A1 | 4/2011 | Wu |
| 2013/0165766 A1 | 6/2013 | Nishikawa |
| 2013/0307566 A1 | 11/2013 | Malone |
| 2016/0242672 A1* | 8/2016 | Mikoshiba ............ A61B 5/165 |
| 2017/0071499 A1 | 3/2017 | Nebuya |
| 2017/0303991 A1 | 10/2017 | Rubinsky |
| 2019/0033974 A1 | 1/2019 | Mu |
| 2019/0125439 A1 | 5/2019 | Rohl |
| 2019/0187223 A1 | 6/2019 | Lacouture |
| 2019/0298202 A1* | 10/2019 | Nakamura ......... G01R 33/0206 |
| 2019/0320981 A1* | 10/2019 | Kodama ............ A61B 5/7221 |
| 2020/0170514 A1 | 6/2020 | Hui |
| 2020/0281490 A1* | 9/2020 | Kataoka ............ G01R 33/0206 |

FOREIGN PATENT DOCUMENTS

| | | | |
|---|---|---|---|
| CN | 108836331 A | 11/2018 | |
| JP | H1199133 A | 4/1999 | |
| JP | 2019045275 A | 3/2019 | |
| JP | 2019045496 A | 3/2019 | |
| KR | 20050005740 A | 1/2005 | |
| WO | 9502360 A1 | 1/1995 | |
| WO | 2010006349 A2 | 1/2010 | |
| WO | 2010113067 A1 | 10/2010 | |
| WO | 2011086512 A1 | 7/2011 | |
| WO | WO-2020040168 A1 * | 2/2020 | .............. A61B 5/05 |
| WO | WO-2020138170 A1 * | 7/2020 | ......... G01R 33/0011 |

OTHER PUBLICATIONS

Li Gang et al., "A New Electrode Mode for Magnetic Detection Electrical Impedance Tomography: Computer Simulation Study", IEEE Transactions on Magnetics, 2012, vol. 48, No. 10, pp. 2543-2550, columns "I. Introduction", "II Magnetic Detection Electrical Impedance Tomography".
Office Action issued for counterpart Taiwanese Application 109117682, issued by the Taiwan Intellectual Property Office on Dec. 8, 2020.
Supplementary International Search Report for International Patent Application No. PCT/JP2020/020202, issued by the Japan Patent Office on Jun. 16, 2021.
Shai Levy et al,"Electromagnetic Impedance Tomography (EMIT):A New Method for Impedance Imaging", 1-14 IEEE Transactions on Medical Imaging, IEEE Service Center, Piscataway, NJ, US, vol. 21, No. 6, Jun. 1, 2002 (Jun. 1, 2002),PP676-687 XP011076308, ISSN: 0278-0062.
Ireland R H et al,"Towards magnetic detection electrical impedance tomography:data acquisition and image reconstruction of current density in phantoms and in vivo; Magnetic detection EIT", Physiological Measurement, Institute of Physics Publishing, Bristol, GB, vol. 25, No. 3, Jun. 1, 2004 (Jun. 1, 2004), pp. 775-796, XP020074156, ISSN: 0967-3334, DOI:10.1088/0967-3334/25/3/016.

* cited by examiner

MEASURING APPARATUS, MEASURING METHOD AND RECORDING MEDIUM

The contents of the following Japanese patent application(s) are incorporated herein by reference:
   2019-103194 filed in JP on May 31, 2019; and
   PCT/JP2020/020202 filed in WO on May 21, 2020.

BACKGROUND

1. Technical Field

The present invention relates to a measuring apparatus, a measuring method and a recording medium.

2. Related Art

Conventionally, there have been methods of acquiring tomographic images and other data for the diagnosis of living bodies (see Patent Documents 1-3). One such method is electro-impedance tomography (EIT), in which a plurality of electrodes are arranged around a living body, and the distribution of electrical conductivity in the living body is detected by the potential difference between other electrodes measured by passing a current through them, and an image of a cross section of the living body is obtained from the distribution.

Patent Document 1: The specification of the U.S. Patent Application Publication No. 2017/0303991.
Patent Document 2: International Publication WO No. 2011/086512.
Patent Document 3: International Publication WO No. 2010/113067.

DESCRIPTION OF EXEMPLARY EMBODIMENTS

Hereinafter, the present invention will be described through embodiments of the invention, but the following embodiments do not limit the invention according to the claims. Moreover, not all combinations of features described in the embodiments are necessary to solutions of the invention.

Figure 1:
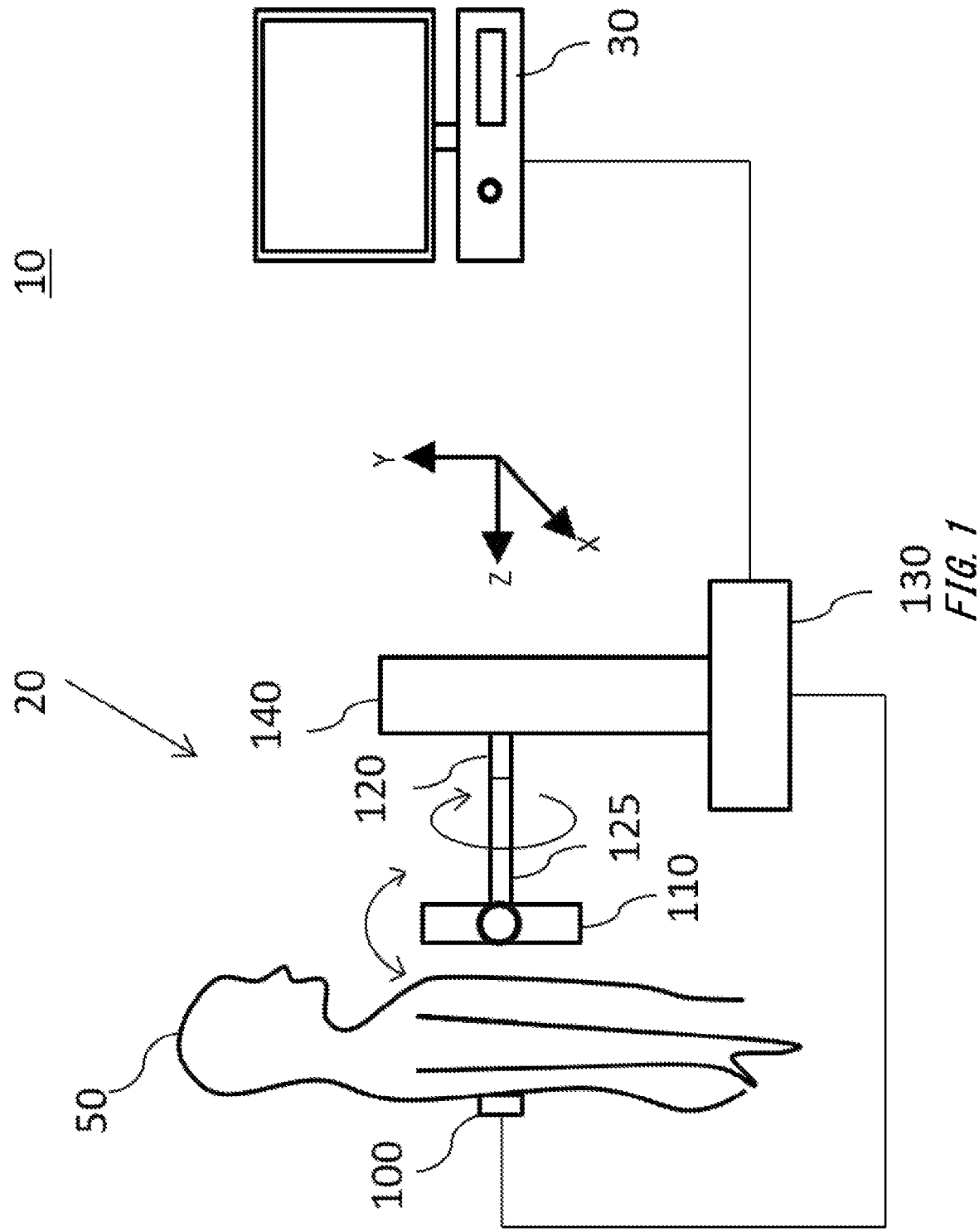
FIG. 1 illustrates a configuration of a measuring apparatus 10 according to the present embodiment.

FIG. 1 illustrates a configuration of a measuring apparatus according to the present embodiment. The measuring apparatus 10 measures the magnetic field generated by applying a current to flow in a living body 50, such as a test subject, and uses the measured magnetic field to estimate the current in the living body 50. The measuring apparatus 10 may be used to acquire the cross sectional image of the living body 50.

The measuring apparatus 10 includes a main body 20 and an information processing section 30. The main body 20 is a component for applying a current to flow in the living body 50 and sensing a magnetic field, including a current applying section 100, a magnetic sensor unit 110, a head 120, a driving section 125, a base section 130 and a pole section 140.

The current applying section 100 is arranged in contact with a surface of the living body 50, and applies a current to flow in the living body 50 during measurement. The magnetic sensor unit 110 is arranged in a position facing a measuring target of the living body 50 (the lung of the test subject as one example) and senses the magnetic field from the living body 50 during measurement. The head 120 supports the magnetic sensor unit 110 and faces the magnetic sensor unit 110 to the living body 50. The driving section 125 is provided between the magnetic sensor unit 110 and the head 120, and changes the orientation of the magnetic sensor unit 110 relative to the head 120 when performing calibration. The driving section 125 according to the present embodiment includes a first actuator that can cause the magnetic sensor unit 110 to rotate 360 degrees about a Z axis in the drawing and a second actuator that causes the magnetic sensor unit 110 to rotate about an axis perpendicular to the Z axis (an X axis for the state in the drawing), and changes the azimuth angle and zenith angle of the magnetic sensor unit 110 using these actuators. Note that the magnetic sensor unit 110 may further be rotatable around the measuring target about the Y axis in the drawing.

The base section 130 is a platform for supporting other members. The test subject, which is the living body 50, may stand on the base section 130, or may sit in front of the base section 130 during measurement. The pole section 140 supports the head 120 at the height of the measuring target of the living body 50. The pole section 140 may be stretchable in order to adjust the height of the magnetic sensor unit 110 in the up-down direction according to the height of the measuring target of the living body 50.

The information processing section 30 is a component for processing measurement data obtained by the main body 20 and outputting this data through printing, displaying, or the like. The information processing section 30 may be a computer such as a PC (personal computer), a tablet computer, a smartphone, a workstation, a server computer, or a general-purpose computer, or may be a computer system in which a plurality of computers are connected. Alternatively, the information processing section 30 may be a dedicated computer designed for specific information processing, or may be a dedicated hardware realized by the dedicated circuit.

Figure 2:
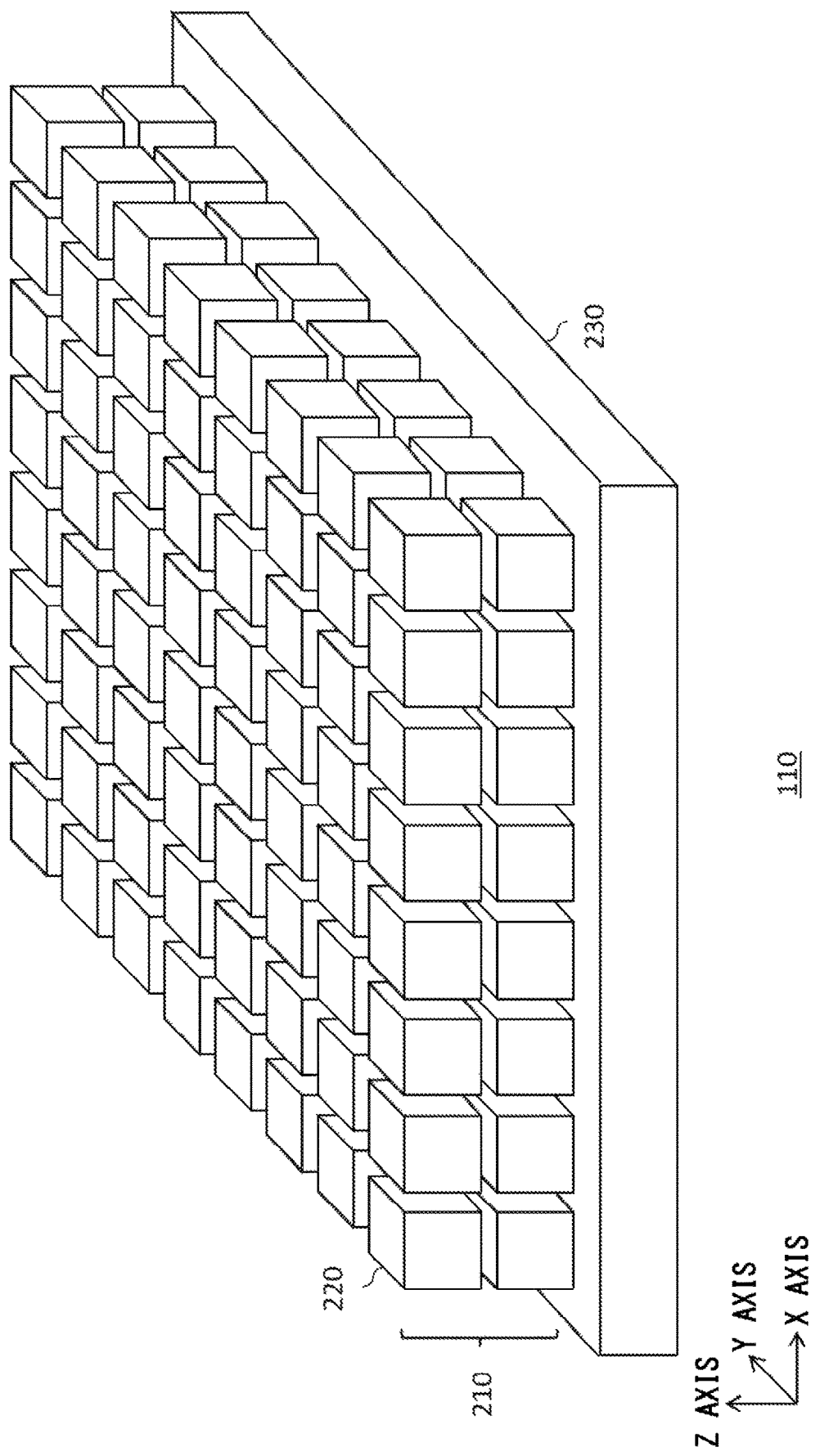
FIG. 2 illustrates a configuration of a magnetic sensor unit 110 according to the present embodiment.

FIG. 2 illustrates a configuration of the magnetic sensor unit 110 according to the present embodiment. The magnetic sensor unit 110 includes a magnetic sensor array 210 and a sensor data gathering section 230. The magnetic sensor array 210 is configured by a three-dimensional array of a plurality of magnetic sensor cells 220 that can detect magnetic fields in three axial directions. The plurality of magnetic sensor cells 220 includes a plurality of magnetic sensors respectively having, as one example, a magnetoresistive element and a magnetic flux concentrator, which is arranged on at least one of one end and the other end of the magnetoresistive element. Note that, preferably, the magnetic flux concentrators are arranged on both ends of the magnetoresistive element, so that sampling of a spatial distribution of the magnetic field described below can be implemented with a higher accuracy. In this drawing, the plurality of magnetic sensor cells 220 in the magnetic sensor array 210 are arranged in a planar shape, in each of the X direction, the Y direction, and the Z direction (for example, a total of 128 magnetic sensor cells 220 with 8 cells arranged in the X direction, 8 cells arranged in the Y direction, and 2 cells arranged in the Z direction).

The sensor data gathering section 230 is electrically connected to the plurality of magnetic sensor cells 220 included in the magnetic sensor array 210 (not illustrated), gathers and processes the measurement data (detection signals) from the plurality of magnetic sensor cells 220 to supply them to the information processing section 30.

Figure 3:
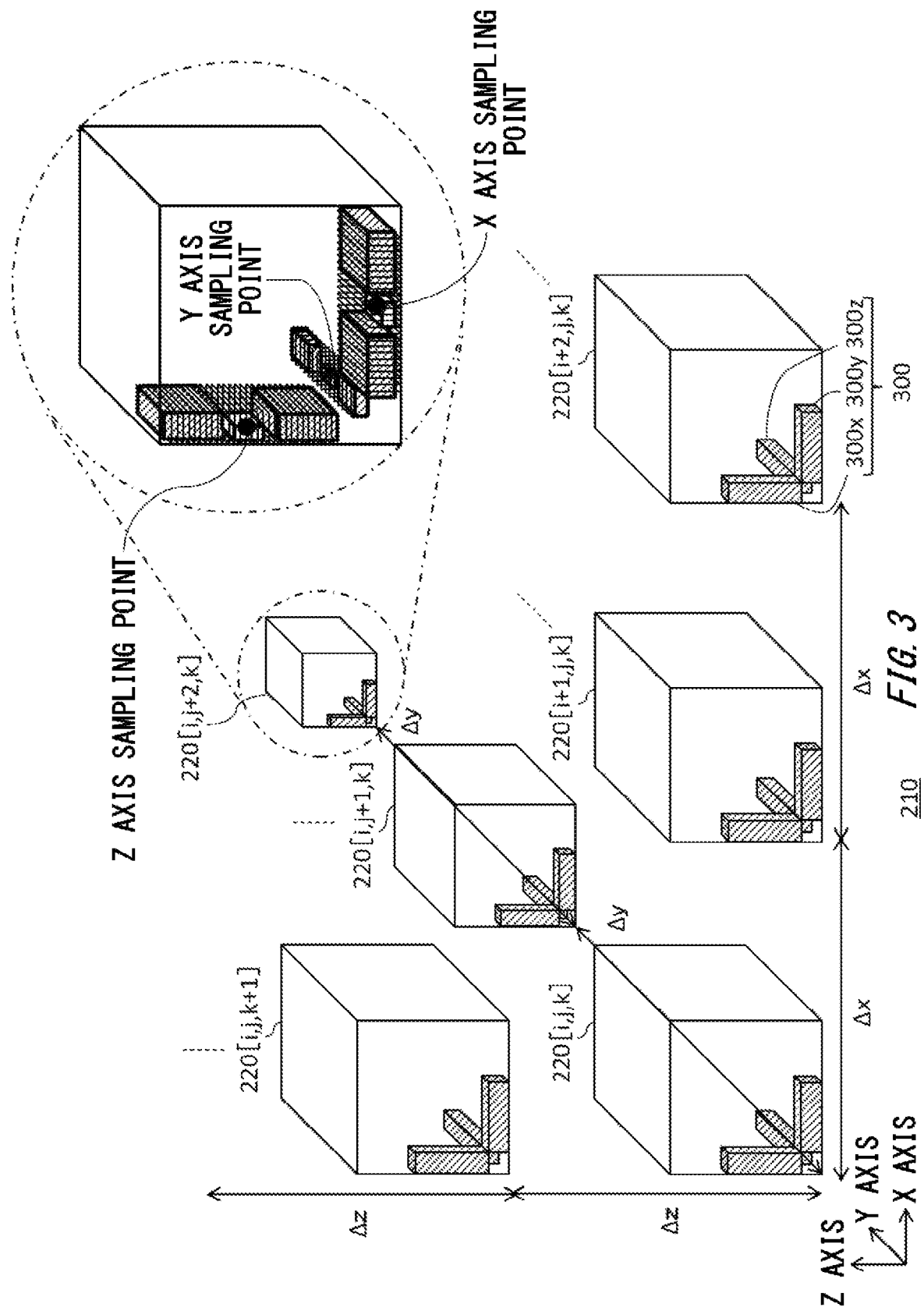
FIG. 3 illustrates a configuration and an arrangement of a magnetic sensor cells 220 in a magnetic sensor array 210 according to the present embodiment.

FIG. 3 illustrates a configuration and an arrangement of the magnetic sensor cells 220 in the magnetic sensor array 210 according to the present embodiment. Each magnetic sensor cell 220 includes a plurality of sensor sections 300x to z (hereinafter, collectively referred to as a "sensor section 300") each including a magnetoresistive element. In the present embodiment, the sensor sections 300x are arranged along the X axis direction and are capable of detecting a magnetic field in the X axis direction. Also, the sensor sections 300y are arranged along the Y axis direction and are capable of detecting a magnetic field in the Y axis direction. Also, the sensor sections 300z are arranged along the Z axis direction and are capable of detecting a magnetic field in the Z axis direction. As illustrated in an enlarged view shown in a dash-dot line part of this drawing, in the present embodiment, the sensor sections 300 each have the magnetic flux concentrators arranged on both ends of the magnetoresistive element. Thus, each sensor section 300 uses the magnetoresistive element arranged in a narrow position sandwiched between the magnetic flux concentrators to perform the sampling of the spatial distribution of the magnetic field, so that spatial sampling points can be clarified in each axis direction. Details about the configuration of each sensor section 300 are described below.

The plurality of magnetic sensor cells 220 are arranged at regular intervals $\Delta x$, $\Delta y$, and $\Delta z$, respectively along the X axis direction, the Y axis direction, and the Z axis direction. The position of each magnetic sensor cell 220 in the magnetic sensor array 210 is expressed by a set [i, j, k] of a position i in the X direction, a position j in the Y direction, and a position k in the Z direction. Herein, i is an integer satisfying $0 \leq i \leq Nx-1$ (Nx represents the number of magnetic sensor cells 220 arranged in the X direction), j is an integer satisfying $0 \leq j \leq Ny-1$ (Ny represents the number of magnetic sensor cells 220 arranged in the Y direction), and k is an integer satisfying $0 \leq k \leq Nz-1$ (Nz represents the number of magnetic sensor cells 220 arranged in the Z direction).

In this drawing, the three axial directions of the magnetic field detected by the sensor sections 300x, 300y, and 300z are the same direction as those of the three dimensions in which the magnetic sensor cells 220 are arranged. Therefore, it is easy to understand each component of the distribution of the measured magnetic field. In addition, in each magnetic sensor cell 220, the sensor sections 300x, 300y and 300z are not overlapped with each other when seeing from each of the three-dimensional directions along which the magnetic sensor cells 220 are arranged, and are preferably arranged to extend in each axial direction of the three axial directions so that one end is provided on the gap side provided between the plurality of sensor sections 300 and the other end is separated from the gap. As one example, this drawing illustrates an example where an air space (gap) is provided at the lower left corner section in front view of the magnetic sensor cell 220, and the sensor sections 300x, 300y, and 300z are arranged to respectively extend in the X axis, the Y axis, and the Z axis directions, so that one end of each sensor section is provided in contact with the air space and the other end is away from the air space. In this drawing, the sensor sections 300x, 300y, and 300z are arranged along three sides orthogonal to each other from one corner section of the magnetic sensor cell 220 having a cubic shape, with an air space provided at the one corner section. Also preferably, coils or magnetic materials of the sensor sections 300x, 300y, and 300z described later are arranged without overlapping with each other. With this arrangement, the measurement points can be clarified, so that each component of the measured magnetic field is recognized more easily. Also, the cross-axis sensitivities of the sensor sections 300x, 300y and 300z can further be seemed to be equivalent to each other, making the calibration calculation of the linear algebra described below become easier. The cross-axis sensitivities result from mutual interference between the coils or the magnetic materials of the sensor sections 300x, 300y, and 300z. However, the three axial directions in which the magnetic field is detected may be different from the three dimensional directions in which the magnetic sensor cells 220 are arranged. When these directions are different from each other, no restriction on the arrangement of the sensor sections 300 in the magnetic sensor cells 220 and the arrangement direction of the magnetic sensor cells 220 can increase the degree of freedom in design of the magnetic sensor array 210.

Figure 4:
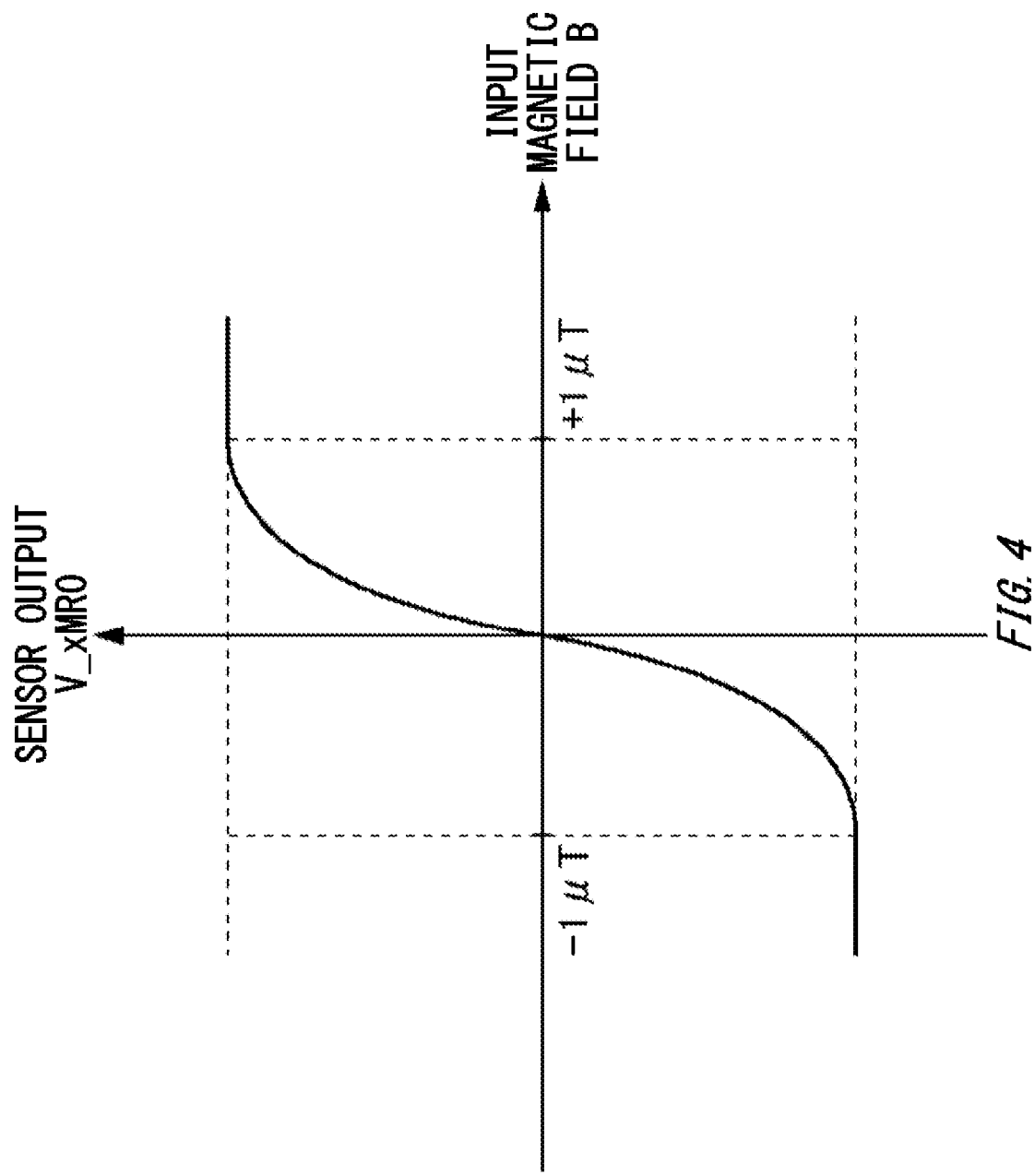
FIG. 4 illustrates one example of an input/output characteristic of the magnetic sensor, which has a magnetoresistive element according to the present embodiment.

FIG. 4 illustrates one example of input/output characteristic of the magnetic sensor included in the magnetoresistive element according to the present embodiment. In this drawing, the horizontal axis indicates a magnitude B of an input magnetic field that is input to the magnetic sensor, and the vertical axis indicates a magnitude V_xMR0 of a detection signal of the magnetic sensor. For example, the magnetic sensor includes a Giant Magneto-Resistance (GMR) element, a Tunnel Magneto-Resistance (TMR) element, or the like, and detects the magnitude of the magnetic field in one predetermined axial direction.

Such a magnetic sensor has high magnetic sensitivity, which is the slope of the detection signal V_xMR0 relative to the input magnetic field B, and can detect a very small magnetic field of approximately 10 pT. On the other hand, the detection signal V_xMR0 becomes saturated when the absolute value of an input magnetic field B is approximately 1 T, for example, and the magnetic sensor has a narrow range in which the linearity of the input/output characteristic is good. Therefore, when a closed loop, which generates a feedback magnetic field, is added to such a magnetic sensor, it is possible to improve the linearity of the magnetic sensor. The following describes such a magnetic sensor.

Figure 5:
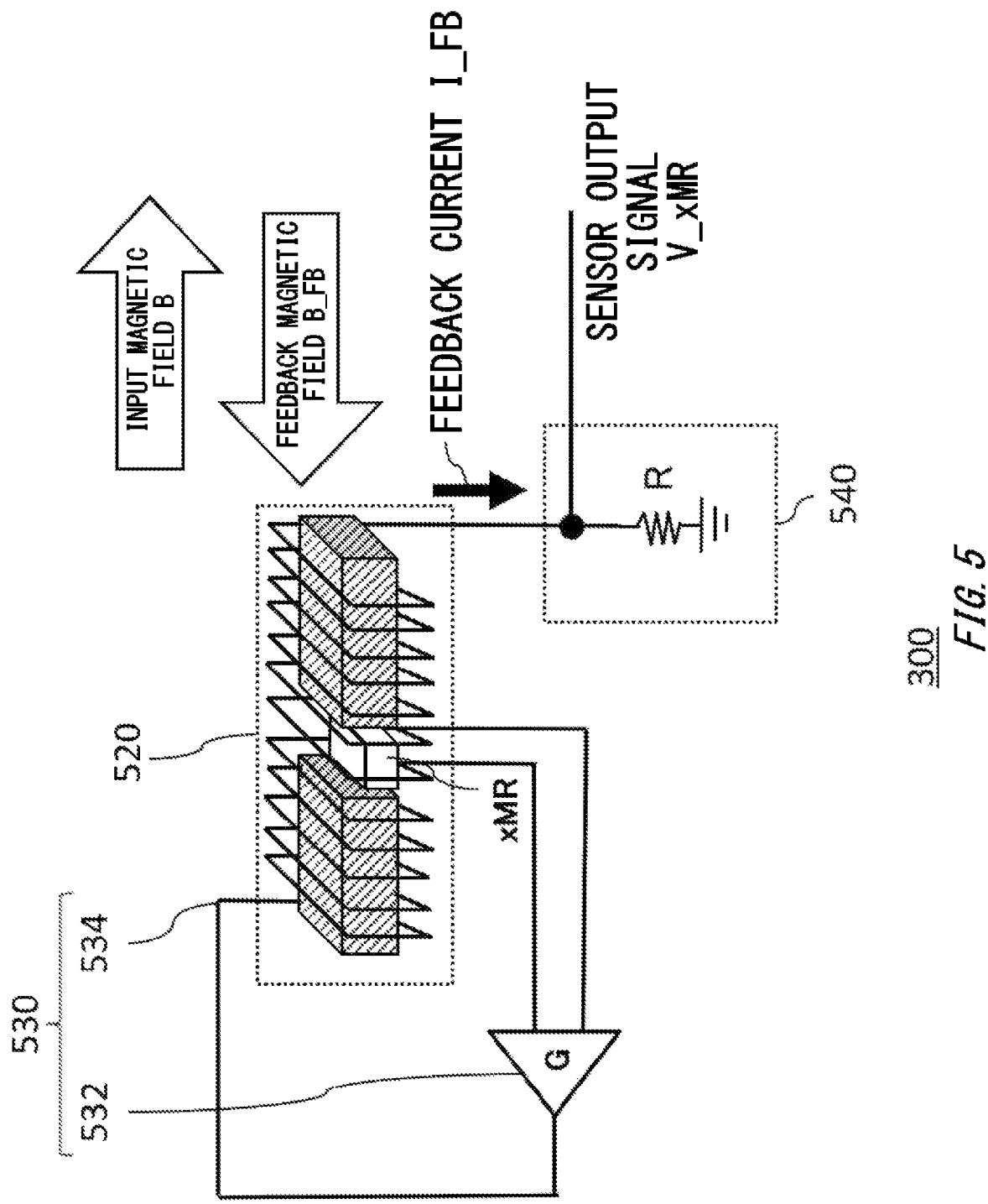
FIG. 5 illustrates a configuration example of a sensor section 300 according to the present embodiment.

FIG. 5 illustrates a configuration example of the sensor section 300 according to the present embodiment. The sensor sections 300 are provided in each of the plurality of magnetic sensor cells 220, and include a magnetic sensor 520, a magnetic field generating section 530, and an output section 540. Note that, a part of the sensor section 300, for example, an amplifier circuit 532 and the output section 540, may be provided on the side of the sensor data gathering section 230 rather than on the side of the magnetic sensor cells 220.

The magnetic sensor 520 includes a magnetoresistive element such as a GMR element or a TMR element, similar to the magnetic sensor described in FIG. 4. In addition, the magnetic sensor 520 further includes magnetic flux concentrators arranged on both ends of the magnetoresistive element. When a positive direction of the magnetosensitive axis is defined as a +X direction, the magnetoresistive element of the magnetic sensor 520 may be formed so that a resistance value increases in response to an input of a magnetic field in a +X direction and the resistance value decreases in response to an input of a magnetic field in a −X direction. Thus, observing a change in the resistance value of the magnetoresistive element of the magnetic sensor 520 can detect the magnitude of the magnetic field B input to the magnetic sensor 520. For example, when the magnetic sensitivity of the magnetic sensor 520 is S, the detection result of the magnetic sensor 520 for the input magnetic field B can be calculated as S×B. Note that as one example, the magnetic sensor 520 is connected to a power source or the like, and outputs a voltage drop corresponding to the change of the resistance value, as a detection result of the input magnetic field. Details about the configuration of the magnetic sensor 520 are described below.

The magnetic field generating section 530 provides a feedback magnetic field for reducing the input magnetic field detected by the magnetic sensor 520, to the magnetic sensor 520. For example, the magnetic field generating section 530 operates to cause the generation of a feedback magnetic field B_FB having an orientation that is the opposite of the orientation of the magnetic field B input to the magnetic sensor 520 and an absolute value that is substantially the same as that of the input magnetic field, to cancel out the input magnetic field. The magnetic field generating section 530 includes the amplifier circuit 532 and a coil 534.

The amplifier circuit 532 outputs, as a feedback current I_FB, a current corresponding to the detection result of the input magnetic field of the magnetic sensor 520. When the magnetoresistive element of the magnetic sensor 520 is configured by a bridge circuit including at least one magnetoresistive element, an output of the bridge circuit is connected to each of a pair of input terminals of the amplifier circuit 532. Then the amplifier circuit 532 outputs a current corresponding to the output of the bridge circuit, as the feedback current I_FB. The amplifier circuit 532 includes a transconductance amplifier, for example, and outputs the feedback current I_FB corresponding to the output voltage of the magnetic sensor 520. For example, when a voltage-current conversion coefficient of the amplifier circuit 532 is G, the feedback current I_FB can be calculated as G×S×B.

The coil 534 generates a feedback magnetic field B_FB corresponding to the feedback current I_FB. The coil 534 is wound to surround the magnetoresistive element and the magnetic flux concentrators arranged on both ends of the magnetoresistive element of the magnetic sensor 520. The coil 534 preferably generates the feedback magnetic field B_FB to be uniform across the entire magnetic sensor 520. For example, when a coil coefficient of the coil 534 is D, the feedback magnetic field B_FB can be calculated as $\beta \times I\_FB$. Herein, the feedback magnetic field B_FB is generated with an orientation that cancels out the input magnetic field B, and therefore the magnetic field input to the magnetic sensor 520 is reduced to B−B_FB. Accordingly, the feedback current I_FB is illustrated by the expression below.

$$I\_FB = G \times S \times (\beta - \beta \times I\_FB) \qquad \text{[Expression 1]}$$

When Expression 1 is solved for the feedback current I_FB, it is possible to calculate the value of the feedback current I_FB in a steady state of the sensor section 300. The expression below is calculated from Expression 1, assuming that the magnetic sensitivity S of the magnetic sensor 520 and the voltage-current conversion coefficient G of the amplifier circuit 532 are sufficiently large.

$$I\_FB = \frac{G \times S \times B}{1 + G \times S \times \beta} \cong \frac{B}{\beta} \qquad \text{[Expression 2]}$$

The output section 540 outputs an output signal V_xMR corresponding to the feedback current I_FB that is to flow in order for the magnetic field generating section 530 to generate the feedback magnetic field B_FB. For example, the output section 540 includes a resistance element with a resistance value R, and outputs a voltage drop, caused by the feedback current I_FB flowing through this resistance element, as the output signal V_xMR. In this case, the output signal V_xMR is calculated from Expression 2 as illustrated in the expression below.

$$V\_xMR = R \times I\_FB = \frac{R \times B}{\beta} \qquad \text{[Expression 3]}$$

As described above, the sensor section 300 generates the feedback magnetic field that reduces the magnetic field input thereto from the outside, and therefore the magnetic field substantially input to the magnetic sensor 520 is reduced. Thus, the sensor section 300 can prevent the detection signal V_xMR from being saturated, for example by using the magnetoresistive element having the characteristic illustrated in FIG. 4 as the magnetic sensor 520, even when the absolute value of the input magnetic field B exceeds 1 T. The following describes the input/output characteristic of such a sensor section 300.

Figure 6:
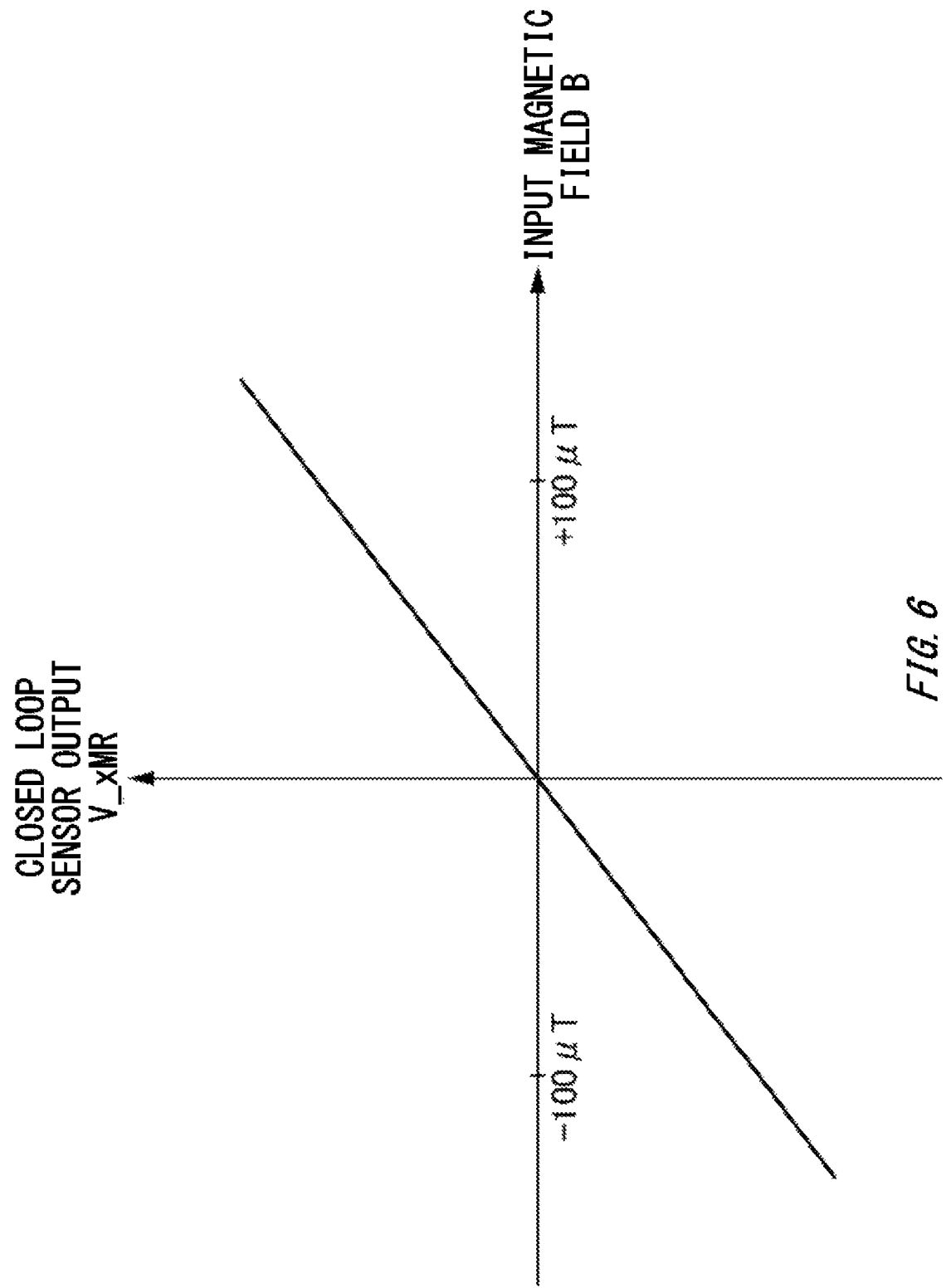
FIG. 6 illustrates one example of an input/output characteristic of the sensor section 300 according to the present embodiment.

FIG. 6 illustrates one example of an input/output characteristic of the sensor section 300 according to the present embodiment. In this drawing, the horizontal axis indicates the magnitude B of the input magnetic field input to the sensor section 300, and the vertical axis indicates the magnitude V_xMR of the detection signal of the sensor section 300. The sensor section 300 has high magnetic sensitivity and can detect a very small magnetic field of approximately 10 pT. The sensor section 300 can also maintain good linearity of the detection signal V_xMR, even when the absolute value of the input magnetic field B exceeds 100 T, for example.

In other words, the sensor section 300 according to the present embodiment is configured such that the detection result for the input magnetic field B has linearity in a predetermined range of the input magnetic field B where the absolute value of the input magnetic field B is less than or equal to several hundred T, for example. By using such a sensor section 300, for example, weak magnetic signals from a living body 50 can be detected easily.

Figure 7:
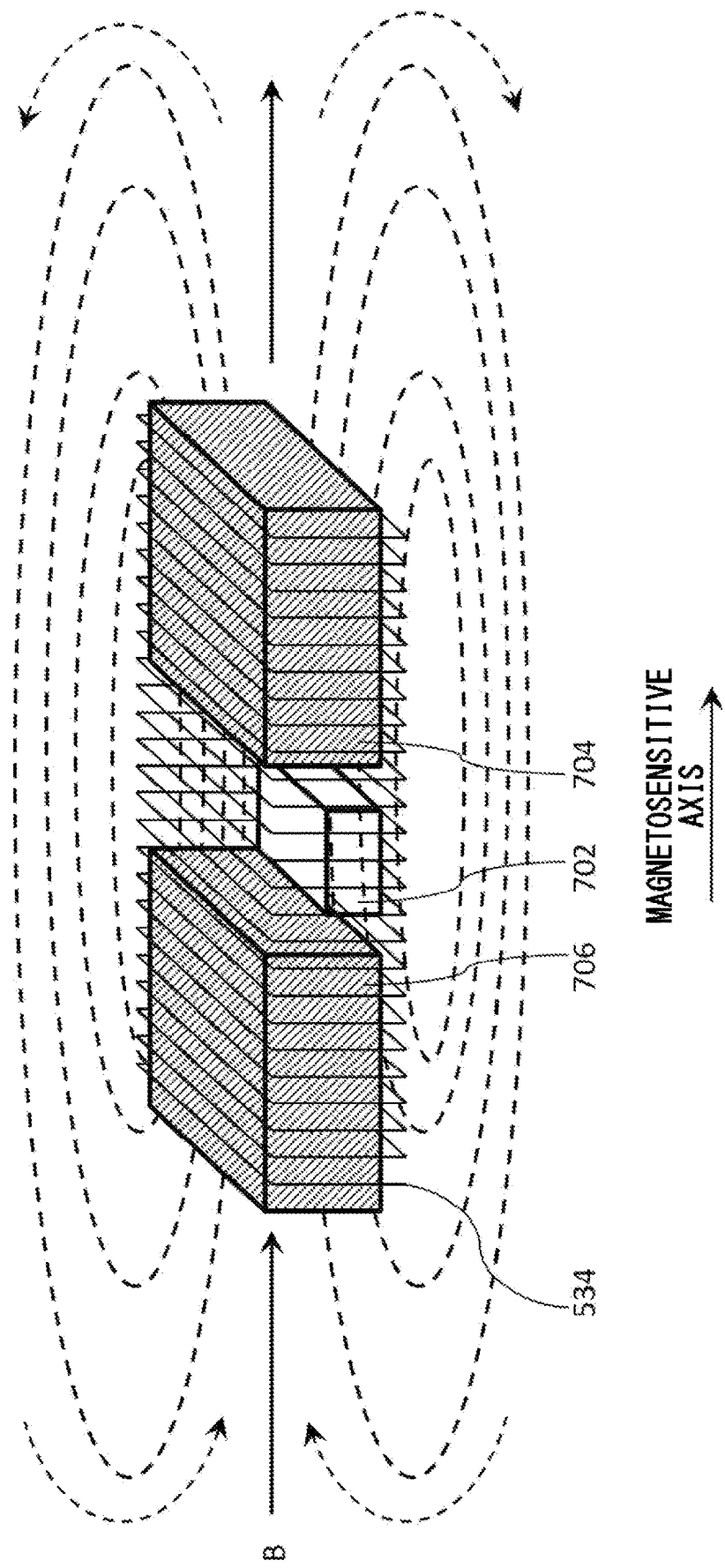
FIG. 7 illustrates a configuration example of a magnetic sensor 520 according to the present embodiment.

FIG. 7 illustrates an example of a configuration example of a magnetic sensor 520 according to the present embodiment. As one example, the magnetic sensor 520 according to the present embodiment includes a magnetoresistive element 702, and magnetic flux concentrators 704 and 706 respectively arranged on one end and the other end of the magnetoresistive element 702. The magnetic flux concentrators 704 and 706 are arranged to sandwich the magnetoresistive element 702. That is, the magnetic flux concentrators are arranged on both ends of the magnetoresistive element 702. In FIG. 7, the magnetic flux concentrator 704 arranged on the right end of the magnetoresistive element 702 along the magnetosensitive axis in front view is a magnetic flux concentrator provided on the positive side of the magnetosensitive axis, and the magnetic flux concentrator 706 arranged on the left end of the magnetoresistive element 702 is a magnetic flux concentrator provided on the negative side of the magnetosensitive axis. Inputting a magnetic field, from the negative side toward the positive side of the magnetosensitive axis, to the magnetic flux concentrators 704 and 706 may increase or decrease the resistance of the magnetoresistive element 702. Note that, the magnetosensitive axis may extend along a magnetization direction fixed by a magnetization fixing layer forming the magnetoresistive element 702. The magnetic flux concentrators 704 and 706 are configured by a soft magnetic material such as iron, for example. Arranging the magnetic flux concentrators 704 and 706 configured by a soft magnetic material respectively on one end and the other end of the magnetoresistive element 702 can increase lines of magnetic force passing through the magnetoresistive element 702, thereby increasing the sensitivity of the magnetic sensor 520.

Note that although this drawing illustrates an example where one end and the other end of the magnetoresistive element 702 are both provided with the magnetic flux concentrators, only either one of one end and the other end of the magnetoresistive element 702 may be provided with a magnetic flux concentrator. However, both one end and the other end of the magnetoresistive element 702 are preferably provided with the magnetic flux concentrators, for the sake of higher sensitivity of the magnetic sensor 520. Furthermore, providing both one end and the other end of the magnetoresistive element 702 with the magnetic flux concentrators clarifies the magnetosensitive section, in other words, because the position of the magnetoresistive element 702 arranged at a narrow position sandwiched by the two magnetic flux concentrators 704 and 706 is to be the magnetosensitive section (spatial sampling point), so that affinity with a signal space separation technique described later can be enhanced more. In this manner, by using a magnetic sensor 520 with magnetic flux concentrators 704 and 706 arranged at both ends of the magnetoresistive element 702 in each sensor section 300, the measuring apparatus 10 according to the present embodiment can sample the spatial distribution of the magnetic field at a very narrow (for example, 100 μm or less) position sandwiched between magnetic flux concentrators at both ends in each axial direction, as shown in FIG. 3, thereby the accuracy of sampling (positional accuracy) is higher than that of sampling the spatial distribution of the magnetic field using a SQUID coil (~2 cm) to measure the biological magnetic field.

Figure 8:
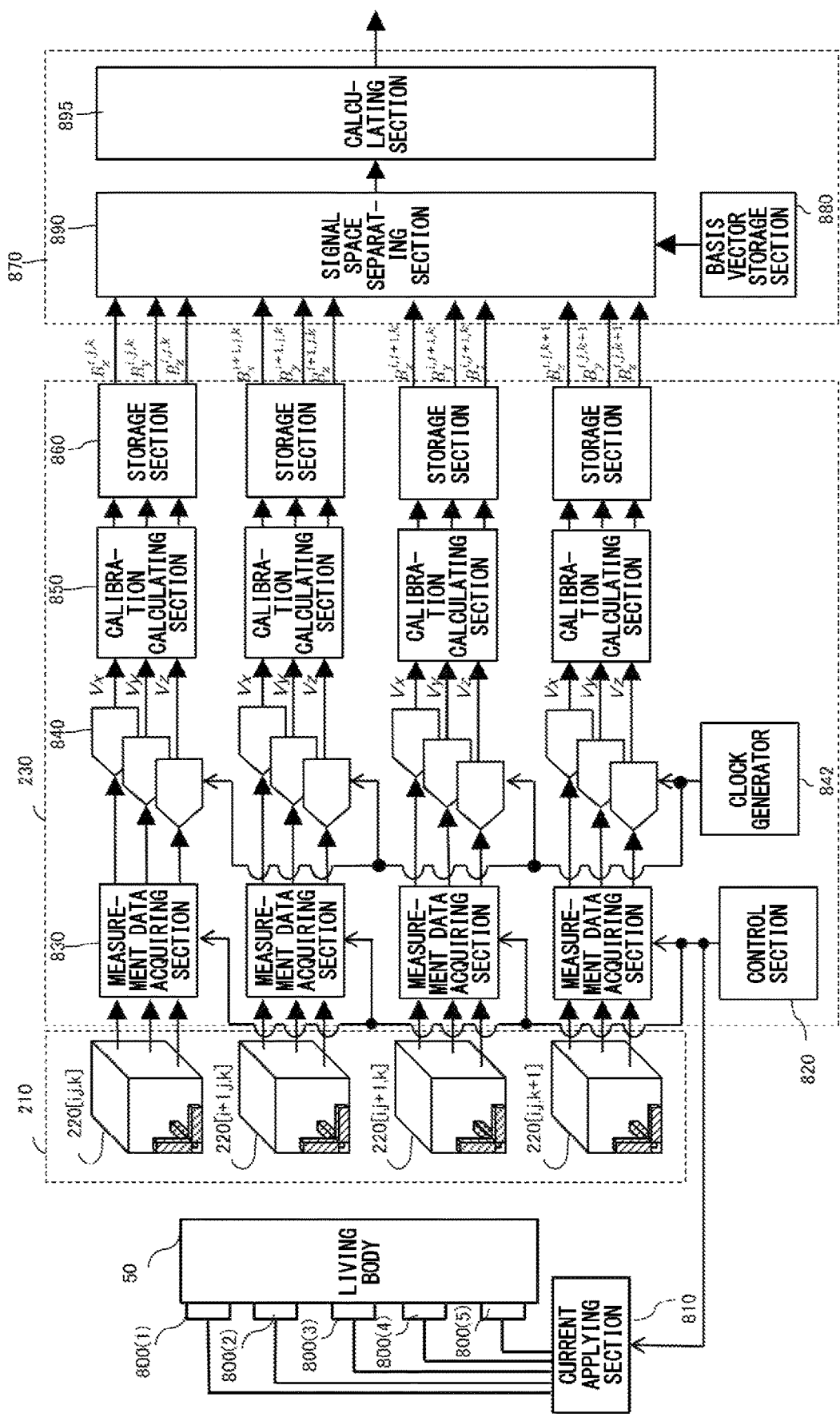
FIG. 8 illustrates a configuration of the measuring apparatus 10 according to the present embodiment.

FIG. 8 illustrates a configuration of the measuring apparatus 10 according to the present embodiment. As an example, the current applying section 100 of the main body 20 shown in FIG. 1 has a plurality of electrodes 800 and a current applying section 810, the magnetic sensor unit 110 has a magnetic sensor array 210 and a sensor data gathering section 230, and the information processing section 30 has an estimation section 870. Note that the electrode unit of this application may include at least a plurality of electrodes 800, for example, which may also be a current applying section 100.

The plurality of electrodes 800 (1) to (5) are electrically connected to the current applying section 810 and are arranged in contact with the position corresponding to the measurement target of the living body 50. The plurality of electrodes 800 may be arranged in a row or in two dimensions on the surface of the living body 50. For example, the plurality of electrodes 800 may be arranged to array in a row in the X axis direction or the Y axis direction of FIG. 1, or may be arranged in a plurality of rows in the X axis direction and the Y axis direction of FIG. 1, respectively. Note that the number of electrodes 800 may be two or more, not specifically limited thereto.

The current applying section 810 is connected to the magnetic sensor unit 110 and applies a current to flow in the living body 50 by at least one electrode pair of the plurality of electrodes 800. The current applying section 810 may apply an alternating current to flow in the living body 50 by at least one electrode pair. The current applying section 810 may have an AC power supply for supplying alternating current to the electrode pairs or may be connected to an external AC power supply. The current applying section 810 may apply a current to flow in the electrode pairs of the plurality of electrodes 800 in response to a synchronization signal from the control section 820 of the magnetic sensor unit 110. The current applying section 810 may, as an example, apply an alternating current of 1 mA or less to flow in the living body 50 in synchronization with a synchronization signal.

The magnetic sensor array 210 has a plurality of magnetic sensor cells 220 and is capable of detecting input magnetic fields in three axial directions at a plurality of positions in the three-dimensional space. Each of the plurality of magnetic sensor cells 220 includes the plurality of sensor sections 300x to z as described above. In this drawing, among the plurality of magnetic sensor cells 220 included in the magnetic sensor array 210 in each dimensional direction, the portions relating to the positions [i, j, k], [i+1, j, k], [i, j+1, k], and [i, j, k+1] are illustrated.

The sensor data gathering section 230 has a control section 820, a plurality of measurement data acquiring sections 830, a plurality of AD converters 840, a clock generator 842, a calibration calculating section 850, and a storage section 860.

The control section 820 is connected to the current applying section 810 and the plurality of measurement data acquiring sections 830, respectively, and controls the synchronous detection of the current applying section 810 and the measurement data acquiring section 830. The control section 820 synchronizes the current flowing to the living body 50 by at least one electrode pair with the acquisition of measurement data by the measurement data acquiring section 830. The control section 820 may output a common synchronization signal to the current applying section 810 and each measurement data acquiring section 830, and the timing of the current application by the current applying section 810 may be matched with the timing of the acquisition of measurement data from each sensor cell by the plurality of measurement data acquiring sections 830. The control section 820 outputs a synchronization signal with a frequency of 10 to 100 KHz as an example.

The plurality of measurement data acquiring sections 830 are connected to the plurality of sensor sections 300x to z of the corresponding magnetic sensor cells 220 and the corresponding AD converters 840, respectively. The measurement data acquiring section 830 acquires measurement data based on the input magnetic field detected by the magnetic sensor cells 220 of the magnetic sensor array 210 from the living body 50 while the current is being applied to flow in the living body 50. The measurement data acquiring section 830 may acquire the measurement data output by the plurality of sensor sections 300x to z of the corresponding magnetic sensor cell 220, respectively, in response to the synchronization signal from the control section 820. The measurement data acquiring section 830 may multiply the measurement data by a synchronization signal and output it. The measurement data acquiring section 830 may further perform low-pass filtering or other processing on the multiplied measurement data.

The plurality of AD converters 840 are connected to the clock generator 842 and the corresponding calibration calculating section 850, respectively, and convert the analog signals (measurement data V_xMR in FIG. 6) acquired by the corresponding measurement data acquiring section 830 into digital measurement data (Vx, Vy, Vz). Herein, Vx, Vy, and Vz are measured values obtained by digitally converting the measurement data from the sensor sections 300x, 300y, and 300z into digital data (for example, digital voltage values).

The clock generator 842 generates a sampling clock and supplies a common sampling clock to each of the plurality of AD converters 840. Each of the plurality of AD converters 840 then performs analog-to-digital conversion in response to a common sampling clock supplied by the clock generator 842. Therefore, all of the plurality of AD converters 840 that perform analog-to-digital conversion of the outputs of the sensor sections 300x to z of the three axes provided at different positions, respectively, operate in synchronization. This enables the plurality of AD converters 840 to concurrently sample the detection results from the three-axis sensor sections 300x to z provided in different spaces.

The plurality of calibration calculating sections 850 are each connected to a corresponding storage section 860, calibrate the measurement data from the AD converter 840 using calibration parameters, and output the calibrated data to the storage section 860. An overview of the calibration for the measurement data performed by the calibration calculating section 850 is as follows. A magnetic field input to the magnetic sensor cell 220 at the position [i, j, k] is defined as B (Bx, By, Bz), and a detection result obtained by the three-axis magnetic sensor using the sensor sections 300x, 300y, and 300z is defined as V (Vx, Vy, Vz). In this case, the detection result V obtained by the three-axis magnetic sensor can be expressed as in the expression below, where matrix S represents the magnetic sensor characteristics of the three-axis magnetic sensor.

$$\begin{pmatrix} Vx \\ Vy \\ Vz \end{pmatrix} = \quad\quad \text{[Expression 4]}$$

$$S\begin{pmatrix} Bx \\ By \\ Bz \end{pmatrix} + \begin{pmatrix} Vos,x \\ Vos,y \\ Vos,z \end{pmatrix} = \begin{pmatrix} Sxx & Sxy & Sxz \\ Syx & Syy & Syz \\ Szx & Szy & Szz \end{pmatrix}\begin{pmatrix} Bx \\ By \\ Bz \end{pmatrix} + \begin{pmatrix} Vos,x \\ Vos,y \\ Vos,z \end{pmatrix}$$

Herein, Sxx, Syy, and Szz represent the sensitivity in the main axis directions of the sensor sections 300x, 300y, and 300z, respectively, and Sxy, Sxz, Syx, Syz, Szx, and Szy represent the sensitivity in the other axis directions. Vos,x, Vos,y, and Vos,z represent the offset in the main axis directions of the sensor sections 300x, 300y, and 300z, respectively. Note that since the detection results of the three-axis magnetic sensor, V (Vx, Vy, Vz), are detected synchronously with the alternating current applied to the living body 50, it is possible to ignore these offsets.

A detection result of each of the sensor sections 300 has linearity for an input magnetic field to be detected within a range of the input magnetic field. Thus, each element of the matrix S becomes a substantially constant coefficient independent of the magnitude of the input magnetic field B. Even when the sensor section 300 has cross-axis sensitivities, each element of the matrix S becomes a substantially constant coefficient independent of the magnitude of the input magnetic field B, as long as the detection result of the sensor section 300 has linearity.

Thus, the calibration calculating section 850 can convert the measurement data V (Vx, Vy, Vz) into the magnetic field measurement data B (Bx, By, Bz) indicating the original input magnetic field by using an inverse matrix $S^{-1}$ of the matrix S and the offset (Vos,x, Vos,y, Vos,z), as in the expression below. Note that this conversion can be also true even when the sensor sections 300x to z have the magnetic flux concentrators described above. This is because the magnetic sensor cell 220 is configured as a three-axis magnetic sensor using the sensor sections 300x to z, and because conversion using linear algebra can be performed.

$$\begin{pmatrix} Bx \\ By \\ Bz \end{pmatrix} = S^{-1}\left\{ \begin{pmatrix} Vx \\ Vy \\ Vz \end{pmatrix} - \begin{pmatrix} Vos,x \\ Vos,y \\ Vos,z \end{pmatrix} \right\} \quad \text{[Expression 5]}$$

The calibration calculating section 850 calculates the inverse matrix $S^{-1}$ of matrix S and the offset (Vos,x, Vos,y, Vos,z) using the environmental magnetic field measurement data, and converts the measurement data acquired by the measurement data acquiring section 830 into measurement data B using these calibration parameters and supplies them to the storage section 860.

As described above, since each sensor section 300 has linearity, the calibration calculating section 850 can convert the measurement data into measurement data B using an substantially constant coefficient. That is, the substantially constant coefficients used by the calibration calculating sections 850 can be defined as a set of calibration parameters using the environment magnetic field data.

The storage section 860 is connected to the estimation section 870, stores the measurement data B calibrated by the calibration calculating section 850, and supplies it to the estimation section 870.

The estimation section 870 estimates the current flowing in the living body 50 based on the measurement data from the storage section 860. The estimation section 870 has a basis vector storage section 880, a signal space separating section 890, and a calculating section 895.

The basis vector storage section 880 is connected to the signal space separating section 890, and stores in advance the basis vectors necessary for the signal space separating section 890 to perform signal separation on the magnetic field measurement data B, and supplies these to the signal space separating section 890.

The signal space separating section 890 is connected to the storage section 860 and the calculating section 895, and separates the spatial distribution of the magnetic field indicated by the measurement data output by the storage section 860 into the magnetic field to be measured from the living body 50 and the disturbance magnetic field. The signal space separating section 890, for example, performs signal separation on the spatial distribution of the magnetic field indicated by the measurement data B with the signal vector, by using, as the basis vector, the signal vector, which is output by each of the plurality of magnetic sensors 520 when the magnetic field with the spatial distribution of the orthonormal function is detected by the magnetic sensor array 210. The signal space separating section 890 obtains the basis vectors required for signal separation from the basis vector storage section 880. Then, the signal space separating section 890 uses the basis vectors obtained from the basis vector storage section 880 to perform signal separation on the spatial distribution of the magnetic field indicated by the measurement data B into the magnetic field to be measured and the disturbance magnetic field, and calculates the magnetic field to be measured by suppressing the disturbance magnetic field. The signal space separating section 890 may calculate and output the magnetic field to be measured at a plurality of magnetic field positions on the surface of the living body 50 where the magnetic sensor array 210 is not arranged.

The calculating section 895 receives the data indicating the magnetic field to be measured from the signal space separating section 890 and calculates the current flowing in the living body 50 based on the magnetic field to be measured. The calculating section 895 may calculate the distribution of the current value in the living body 50 where the current is applied by the electrode pair from the magnetic field to be measured at a plurality of positions on the surface of the living body 50.

Figure 9:
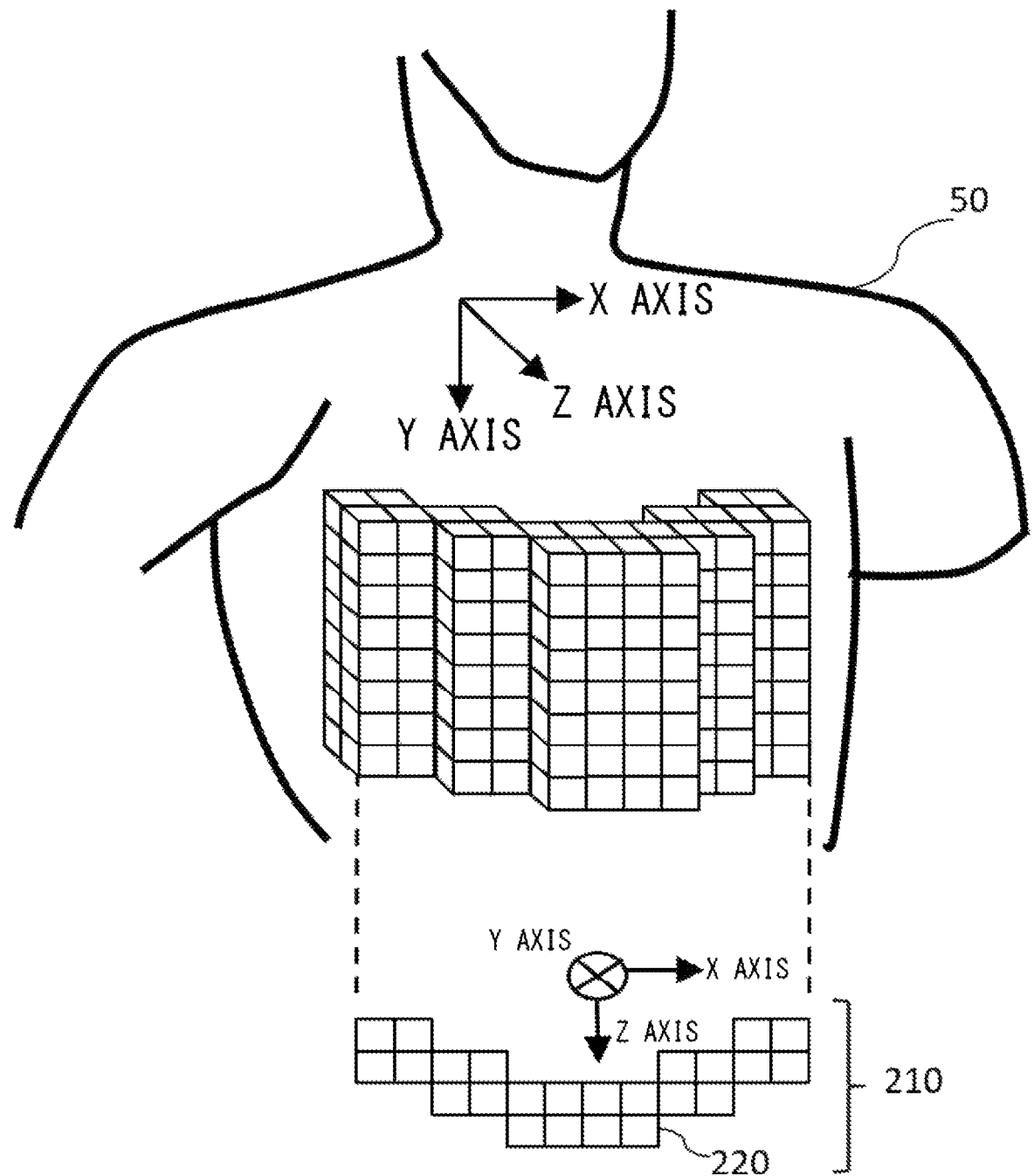
FIG. 9 illustrates an example of measuring a magnetic field using the magnetic sensor array 210 wherein the measuring apparatus 10 of the present embodiment are arranged in a curved surface shape.

FIG. 9 illustrates an example of the measuring apparatus 10 of the present embodiment measuring a magnetic field using a magnetic sensor array 210 arranged in a curved surface shape. The magnetic sensor array 210 has a plurality of magnetic sensor cells 220 in each of the X, Y, and Z directions (for example, 12 in the X direction, 8 in the Y direction, and 2 in the Z direction, for a total of 192 magnetic sensor cells 220) arranged in a curved surface shape. The magnetic sensor cells 220 are arranged at respective grid points included in the curved surface shape in a three-dimensional lattice space. Note that herein, the grid points are points provided at predetermined regular intervals provided along the X direction, the Y direction, and the Z direction to form a lattice form. As one example, each magnetic sensor cell 220 is arranged along a curved surface protruding in a direction orthogonal to any one direction of the X direction, the Y direction, and the Z direction, as viewed in one direction. This drawing illustrates an example where each magnetic sensor cell 220 is arranged along a curved surface protruding in a positive direction of the Z axis as viewed in the Y direction. In this case, for example, the magnetic sensor array 210 may form a curved surface shape protruding in the positive direction of the Z axis, with the respective magnetic sensor cells 220 arranged at the respective grid points in the three-dimensional lattice space while having the respective vertices of the respective magnetic sensor cells 220 arranged in the negative direction of the Z axis as much as possible without exceeding a range of a predetermined curved surface protruding in the positive direction of the Z axis.

The measuring apparatus 10 measures the magnetic field by arranging the magnetic sensor array 210 so that the center position in the Y axis direction coincides with the position where the plurality of electrodes 800 are arranged and the center position in the X axis direction of the living body 50 (such as the chest of the test subject) is arranged at the center of the curved surface. This allows the measuring apparatus 10 to separate the magnetic field to be measured from the disturbance magnetic field with high accuracy by performing signal space separation on the signal space using the measurement data B measured at a position close to the living body 50, which is the source of the magnetic field to be measured. Note that in this case, it is preferable for the magnetic sensor array 210 to have a curvature of the curved surface that is roughly equivalent to the curvature around the test subject's chest, so that the magnetic field can be measured in a position closer to the living body 50, which is the source of the magnetic field to be measured.

Figure 10:
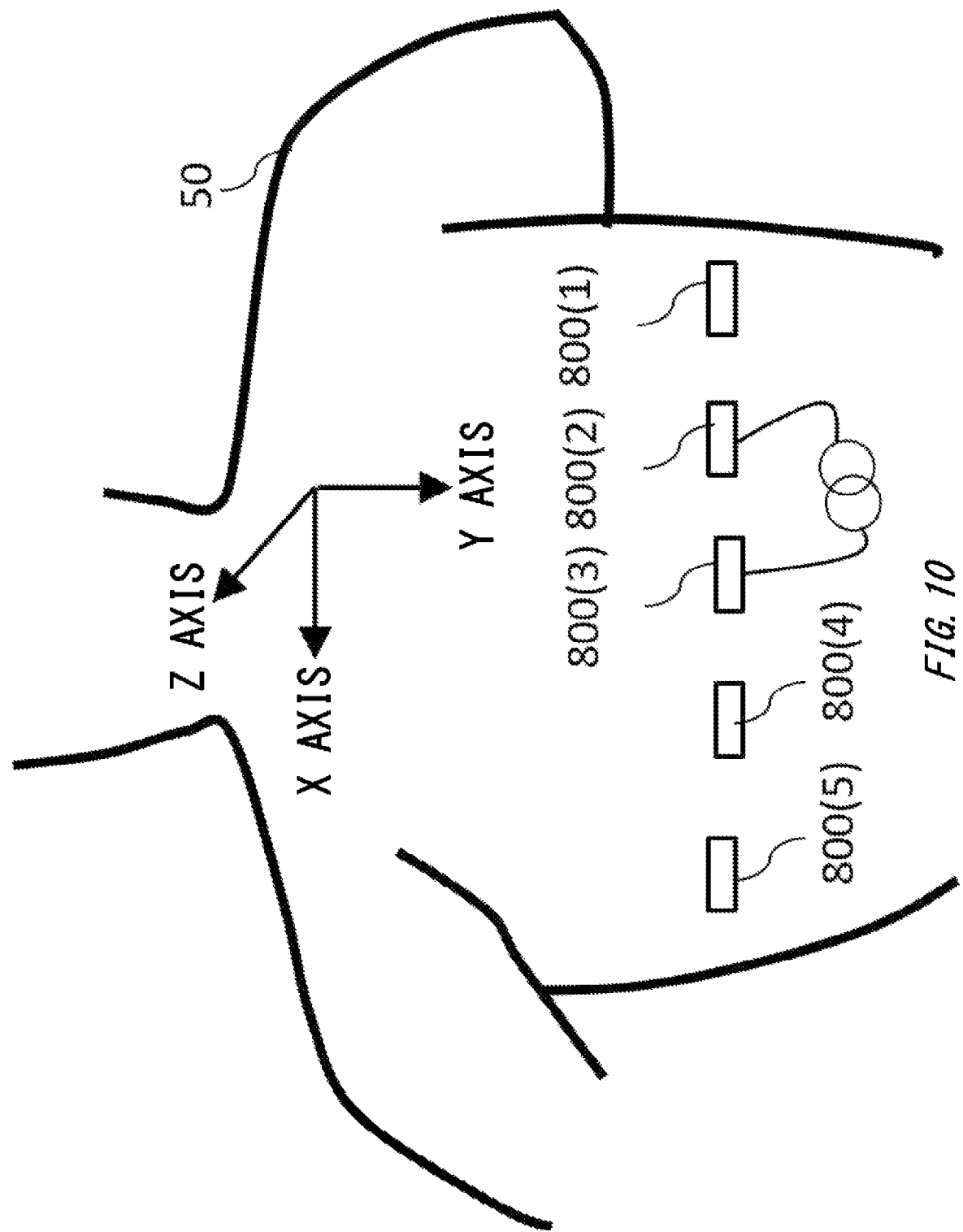
FIG. 10 illustrates an arrangement example of a plurality of electrodes 800 of the measuring apparatus 10 of the present embodiment.

FIG. 10 illustrates an arrangement example of the plurality of electrodes 800 of the measuring apparatus 10 of the present embodiment. The plurality of electrodes 800 (1) to (5) are arranged in a row in the X axis direction in contact with the opposite side of the living body 50 (for example, the back side of the test subject) where the magnetic sensor array 210 is arranged. The plurality of electrodes 800 may be exposed and fixed in a row on a belt, for example, and may be arranged in a state of being in contact with the living body 50 by wrapping and fixing the belt around the living body 50.

Figure 11:
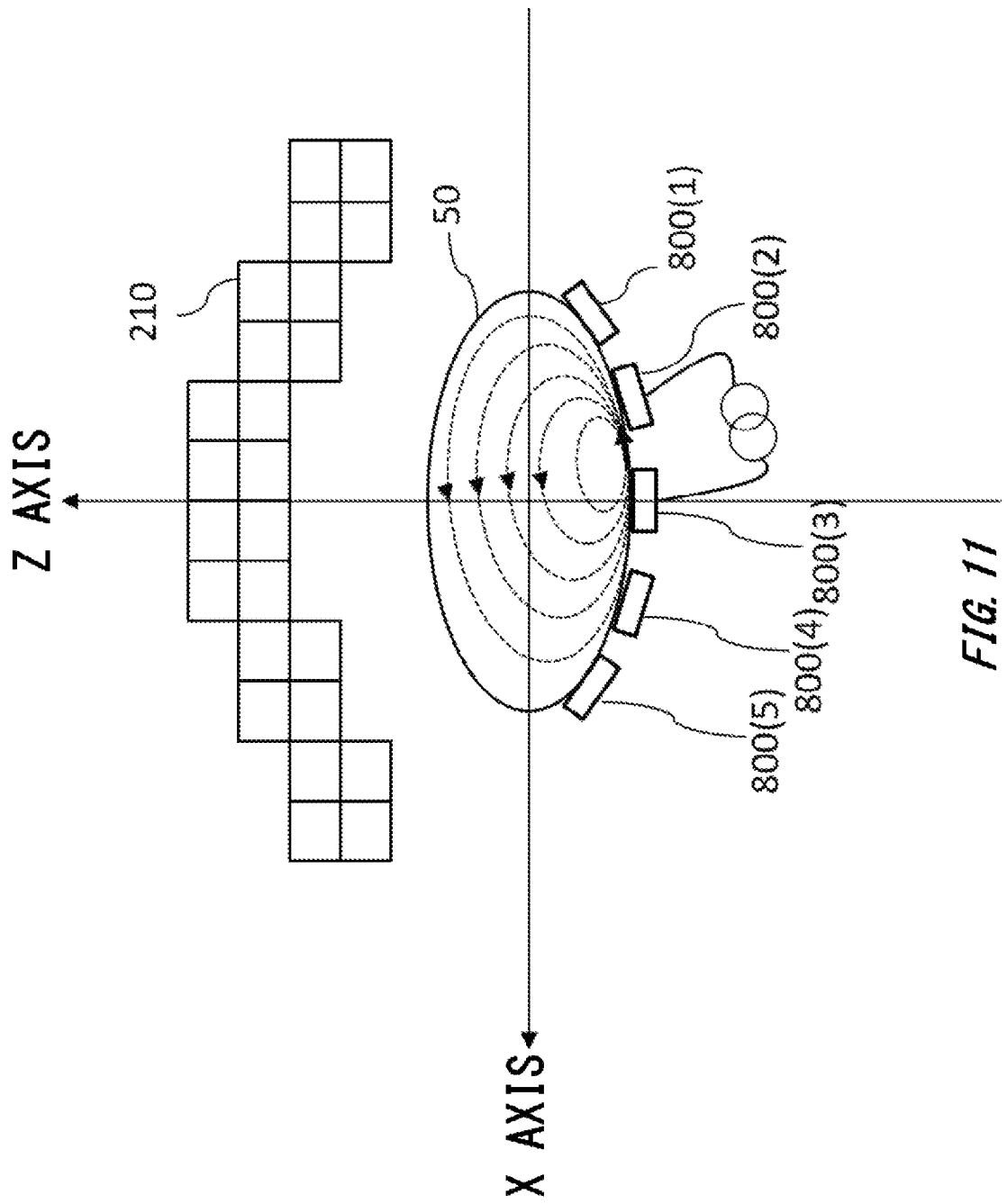
FIG. 11 illustrates an illustration of a cross section parallel to the XZ plane of a part of the measuring apparatus 10 of the present embodiment.

FIG. 11 illustrates a cross section parallel to the XZ plane of a part of the measuring apparatus 10 of the present embodiment. In FIG. 11, the dotted arrows in the living body 50 schematically show the flow of secondary current in the living body 50. In the measuring apparatus 10, the plurality of electrodes 800 contact one side of the living body 50, and the magnetic sensor array 210 detects the input magnetic field at the other side of the living body 50. The measuring apparatus 10 applies an alternating current to an electrode pair consisting of, for example, two electrodes 800 (2) and (3), which causes a secondary current to flow in the living body 50. The measuring apparatus 10 can detect the magnetic field generated during the flow of alternating current by the electrode pair with the magnetic sensor array 210, and calculate the distribution of the current in the living body 50 from the detected magnetic field. Note that the magnetic sensor array 210 is arranged non-contact with the electrode unit including the plurality of electrodes 800, and is arranged opposite to the electrode unit. This allows the magnetic sensor array 210 to efficiently reduce the effect from the current flowing in the electrode unit itself on the magnetic field from the living body 50 to be detected.

Figure 12:
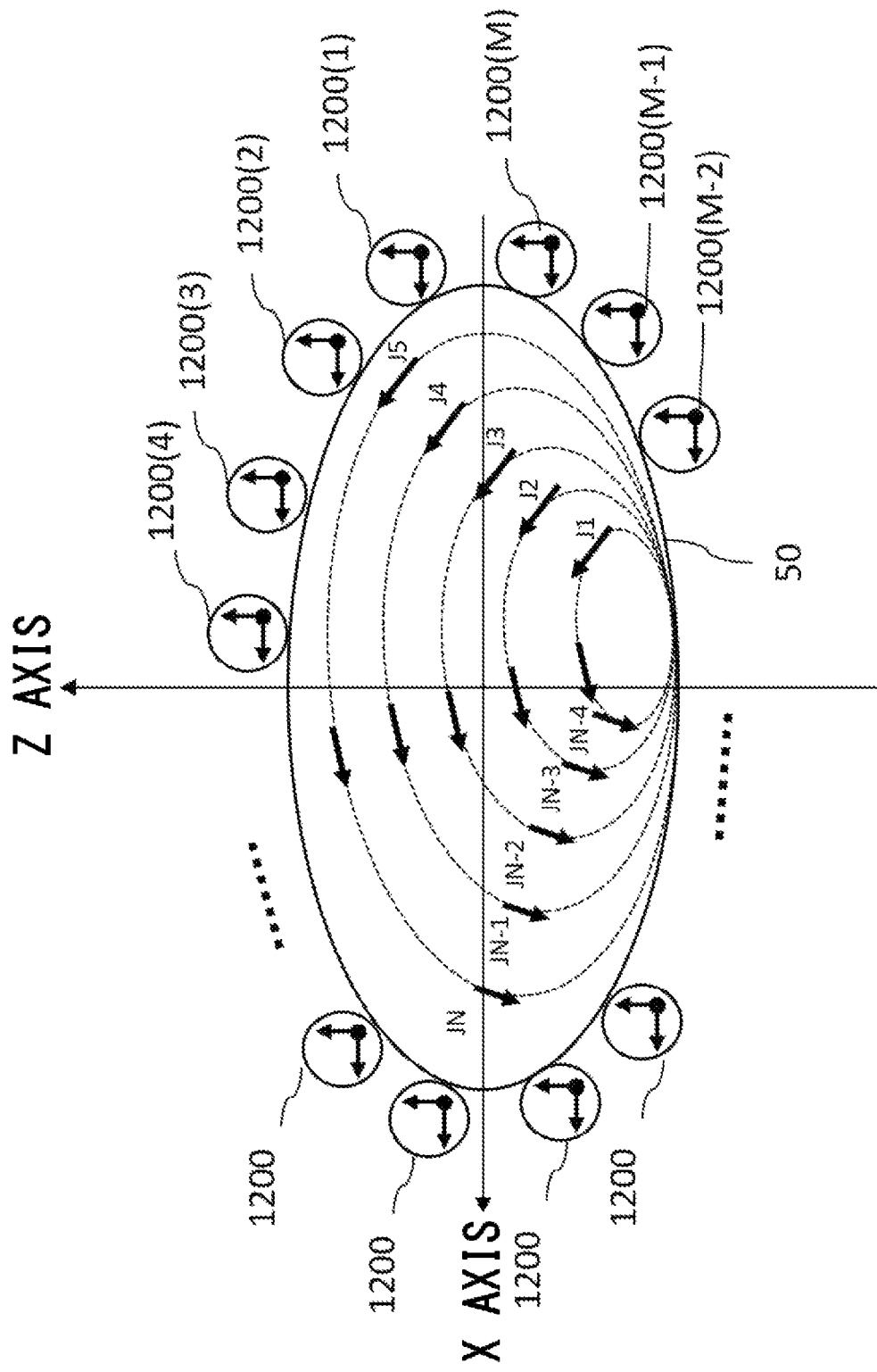
FIG. 12 illustrates a distribution of a magnetic field and current detected by the measuring apparatus 10 of the present embodiment in a cross section parallel to the XZ plane.

FIG. 12 illustrates a distribution of the magnetic field and current detected by the measuring apparatus 10 of the present embodiment in a cross section parallel to the XZ plane. The signal space separating section 890 of the measuring apparatus 10 of this embodiment can calculate the magnetic fields to be measured at M (M≥1) magnetic field positions 1200 on the surface of the living body 50 based on the magnetic fields detected by the magnetic sensor array 210. This allows the calculating section 895 to calculate the currents J1 to JN at N (N≥1) positions (voxels) in the living body 50 using the magnetic fields at said M magnetic field positions 1200. Note that the magnetic field position 1200 may be substantially the same as the position where the plurality of electrodes 800 are arranged in the Y axis direction.

Figure 13:
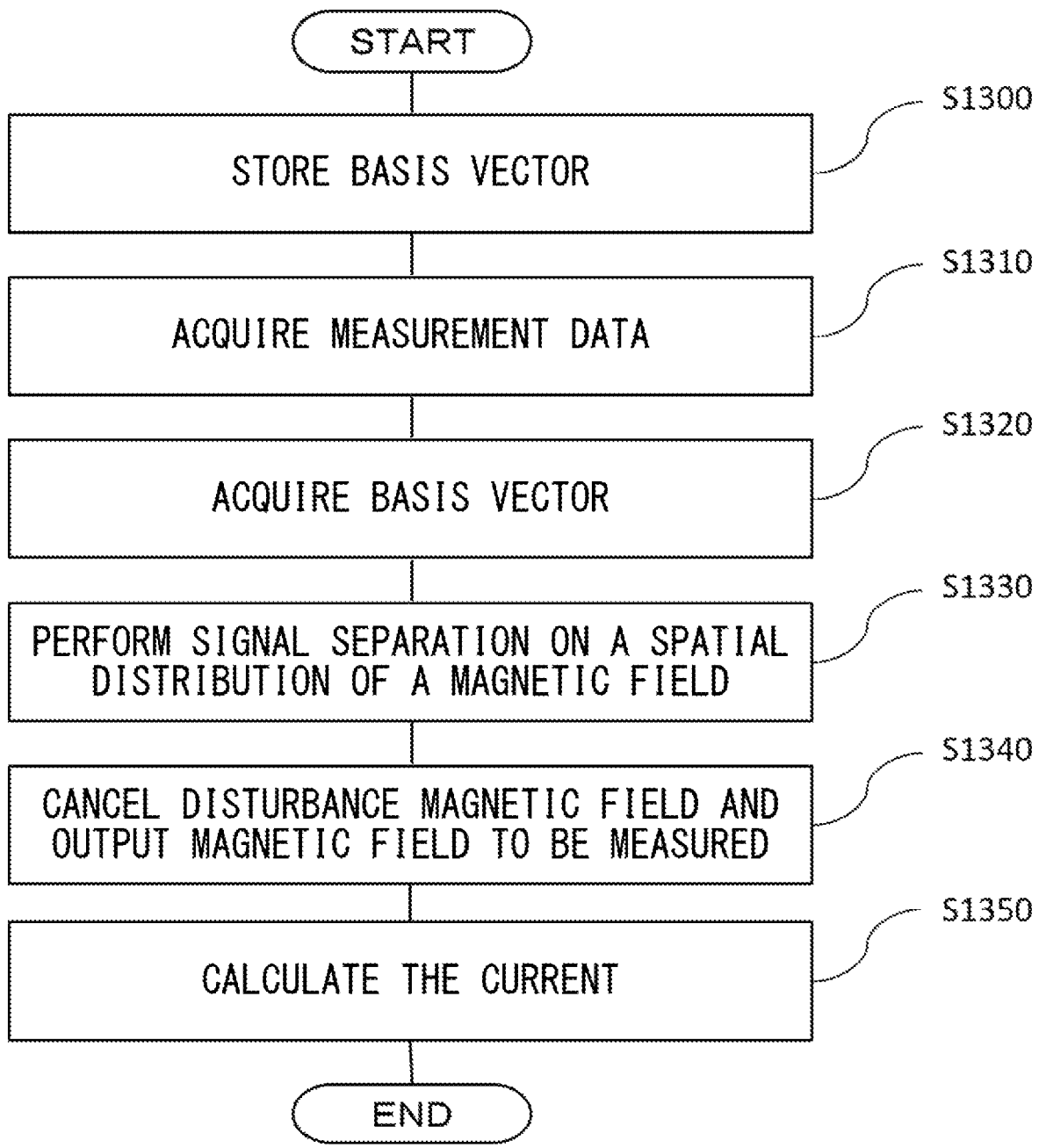
FIG. 13 illustrates a measurement flow of the measuring apparatus 10 according to the present embodiment.

FIG. 13 illustrates a measurement flow of the measuring apparatus 10 according to the present embodiment.

In step 1300, the basis vector storage section 880 stores the basis vectors. As one example, before the measurement of the magnetic field to be measured, the basis vector storage section 880 stores, as the basis vector, a signal vector output from each of the plurality of magnetic sensors 520 when the magnetic sensor array 210 detects a magnetic field having a spatial distribution of spherical harmonics. Specifically, the basis vector storage section 880 stores, as the basis vector, a magnetic field signal vector obtained by spatially sampling the spherical harmonics when a predetermined point in a space is designated as the coordinate origin. Herein, the spherical harmonics is a function obtained by restricting, to a unit sphere, the homogeneous polynomial that is a solution to an n-dimensional Laplace equation, and has orthonormality on the sphere. Note that the basis vector storage section 880 may store the basis vectors before the signal space separation (step 1330) by the measuring apparatus 10. Furthermore, the basis vector storage section 880 may store, as the basis vector, a signal vector predetermined from a simulation result or the like.

Next, in step 1310, the measuring apparatus 10 acquires measurement data based on the input magnetic field detected while the current is applied to the living body 50. The control section 820 may output a synchronization signal to the current applying section 810 and the measurement data acquiring section 830 for synchronous detection. The control section 820 may output a synchronization signal with a frequency set by the user or a predetermined frequency.

The current applying section 810 may apply an alternating current of the same frequency as the synchronization signal to the living body 50 by means of an electrode pair during the period when the synchronization signal is being received, while the measurement data acquiring section 830 may acquire measurement data during the period when the synchronization signal is being received. The current applying section 810 may apply a current to flow in a living body by applying a current to an electrode pair consisting of two adjacent electrodes of the plurality of electrodes 800. For example, the current applying section 810 may apply a current to an electrode pair consisting of two adjacent electrodes 800 in sequence while shifting the electrodes 800 one by one to apply a current to flow in the living body 50. Specifically, the current applying section 810 may switch electrode pairs in the order of electrodes 800 (1) and (2), electrodes 800 (2) and (3), electrodes 800 (3) and (4), and the electrode pair of the electrodes 800 (4) and (5) in FIG. 11 every one or more cycles of the synchronization signal to apply current, and to make the current to flow in the living body 50 from all the combinations of the electrode pairs.

The measurement data acquiring section 830 may acquire the measurement data measured for each electrode pair by multiplying it by a synchronization signal. The measurement data acquiring section 830 may output the measurement data multiplied by the synchronization signal and filtered by an analog low-pass filter.

The plurality of AD converters 840 each perform analog-to-digital conversion of the acquired measurement data and output it. The calibration calculating section 850 may calibrate the acquired measurement data and output it to the storage section 860. The calibration calculating section 850 may filter the measurement data with a digital low-pass filter before calibration. The signal space separating section 890 obtains the calibrated measurement data B from the storage section 860.

In step 1320, the signal space separating section 890 obtains the signal vectors stored as basis vectors by the basis vector storage section 880 in step 1300 from the basis vector storage section 880. Note that in this flow, either one of step 1310 or step 1320 may be performed before the other.

In step 1330, the signal space separating section 890 performs series expansion of the spatial distribution of the magnetic field indicated by the magnetic field measurement data B acquired in step 1310, using the signal vector acquired in step 1320 as the basis vector. The signal space separating section 890 then performs signal separation on the spatial distribution of the magnetic field from the vector obtained by series expansion into the magnetic field to be measured and the disturbance magnetic field. Note that the orthonormal function may be a spherical harmonic function. In addition, the signal space separating section 890 calculates the coefficients of the basis vectors by the least-squares method in separating the signals.

Then, in step 1340, the signal space separating section 890 calculates only the magnetic field to be measured by suppressing the disturbance magnetic field based on the result of the signal separation in step 1330, and outputs it to the calculating section 895. This will be described in detail below.

The static magnetic field B(r) is obtained as the spatial gradient of the potential V(r), using the potential V(r) satisfying the Laplace equation Δ·V(r)=0, as shown in the following expression. Herein, in the expression, r represents a position vector representing the position with respect to the coordinate origin, Δ represents a Laplacian, represents permeability, and ∇ represents a vector differential operator.

$$B(r)=-\mu\cdot\nabla\cdot V(r) \quad\quad [\text{Expression 6}]$$

Generally, a solution to the Laplace equation is in a form of series expansion using spherical harmonics Yl,m(θ,φ) which is an orthonormal function system, and thus the potential V(r) can be expressed as in the expression below. Herein, |r| is the absolute value of the position vector r (distance from the coordinate origin), θ and φ are the two declination angles in spherical coordinates, 1 is the azimuthal quantum number, m is the magnetic quantum number, α and β are the multipole moments, and Lin and Lout are the series numbers for the space in front and the space behind the magnetic sensor array 210, respectively, as seen from the living body 50. The azimuthal quantum number 1 is a positive integer, and the magnetic quantum number m is an integer in a range from −1 to +1. In other words, when 1 is 1, for example, m is −1, 0, and 1, and when 1 is 2, for example, m is −2, −1, 0, 1, and 2. Note that since there is no case of a single magnetic pole in the magnetic field, the azimuthal quantum number 1 starts from 1 instead of 0 in Expression 7. The first term in Expression 7 is inversely proportional to the distance from the coordinate origin and indicates the potential that exists in the space in front of the magnetic sensor array 210 as seen from the living body 50. The second term in Expression 7 is a term proportional to the distance from the coordinate origin and indicates the potential that exists in the space behind the magnetic sensor array 210 as seen from the living body 50.

[Expression 7]
$$V(r) = \sum_{l=1}^{Lin}\sum_{m=-l}^{l} \alpha_{l,m} \cdot \left(\frac{1}{r^{l+1}} \cdot Y_{l,m}(\theta, \phi)\right) + \sum_{l=1}^{Lout}\sum_{m=-l}^{l} \beta_{l,m} \cdot \left(r^l \cdot Y_{l,m}(\theta, \phi)\right)$$

Therefore, according to Expression 6 and Expression 7, the static magnetic field B(r) can be expressed by the expression below. Herein, the first term in Expression 8 indicates the magnetic field source (magnetic field to be measured) that exists in the space in front of the magnetic sensor array 210 as seen by the test subject. The second term in Expression 8 represents the disturbance magnetic field created by the magnetic field source that exists in the space behind the magnetic sensor array 210 as seen from the living body 50.

[Expression 8]
$$B(r) = -\mu \sum_{l=1}^{Lin}\sum_{m=-l}^{l} \alpha_{l,m} \cdot \nabla\left(\frac{1}{r^{l+1}} \cdot Y_{l,m}(\theta, \phi)\right) - $$
$$\mu \sum_{l=1}^{Lout}\sum_{m=-l}^{l} \beta_{l,m} \cdot \nabla\left(r^l \cdot Y_{l,m}(\theta, \phi)\right)$$

When the solution of the Laplace equation is expressed in the form of a series expansion using spherical harmonic functions, the general solution is an infinite series, but it may be sufficient to obtain a sufficient SNR (signal-to-noise ratio, that is, the ratio of the magnetic field signal to be measured to the disturbance magnetic field and sensor noise) to measure the magnetic field from a living body 50, and in practice, it is said that to express with a series of approximately 10 terms is sufficient. Also, for example, it is said that the series of signal space separation in magnetoencephalography may be approximately Lin=8 and Lout=3. Therefore, the case of Lin=8 and Lout=3 will be described as an example in the present embodiment. However, the Lin and Lout values are not limited to this, and may be any numerical values that are sufficient for sufficiently suppressing the disturbance magnetic field and calculating the magnetic field to be measured.

Herein, the vectors representing the magnetosensitive axis directions and magnetic sensitivity of the sensor sections 300x, y, and z in each magnetic sensor cell 220 are defined as nx, ny, and nz, respectively, and al,m and bl,m are defined as transpose matrices with the subscript t as the following expression. That is, al,m and bl,m are defined as vectors that have, as their components, the inner product of nx, ny, nz (each vector representing the magnetosensitive axis directions and the magnetic sensitivity of the sensor sections 300x, y, and z) and the spherical harmonic function, which is a three-dimensional vector signal. This means that in each magnetic sensor cell 220, the spherical harmonic function is sampled in a Cartesian coordinate system. Note that the al,m and bl,m are vectors with dimensions equal to the number of magnetic sensor cells 220 multiplied by three. The respective vectors nx, ny, and nz, which represent the magneto-sensitive axis directions and the magnetic sensitivity of each sensor section 300, may be the vectors corresponding to the sensitivity in the main axis direction and the sensitivity in the other axis directions described above. nx may correspond to Sxx, Sxy, and Sxz. ny may correspond to Syx, Syy, and Syz. nz may correspond to Szx, Szy, and Szz. In this manner, the values of al,m and bl,m calculated including the sensitivity in the main axis directions of the sensor sections 300x, y, and z and the sensitivity correction in the other axis directions are stored in the basis vector storage section 880. The magnetic measuring apparatus 10 according to the present embodiment, in which the basis vector storage section 880 stores the values of al,m and bl,m calculated including the correction of the magnetic sensitivity (main axis sensitivity and cross-axis sensitivities), performs the correction in the calibration calculating section 850 for the acquired measurement data during operation, thereby making it possible to correct the magnetic sensitivity (main axis sensitivity and cross-axis sensitivities) of each magnetic sensor cell 220.

[Expression 9]
$$a_{l,m} = -\mu \cdot \left[\nabla\left(\frac{1}{r^{l+1}} \cdot Y_{l,m}(\theta, \phi)\right)\right]^t \cdot \begin{bmatrix} nx \\ ny \\ nz \end{bmatrix}$$

$$b_{l,m} = -\mu \cdot \left[\nabla\left(r^l \cdot Y_{l,m}(\theta, \phi)\right)\right]^t \cdot \begin{bmatrix} nx \\ ny \\ nz \end{bmatrix}$$

Then, the sensor output vector Φ output by the magnetic sensor cell array 210 at a certain time can be expressed by the following expression.

[Expression 10]
$$\Phi = \sum_{l=1}^{Lin}\sum_{m=-l}^{l} \alpha_{l,m} \cdot a_{l,m} + \sum_{l=1}^{Lout}\sum_{m=-l}^{l} \beta_{l,m} \cdot b_{l,m}$$

Furthermore, Sin, Sout, Xin, and Xout are each defined in the following manner. That is, Sin is defined as vector of total Lin·(Lin+2) column in which each vector a at each integer timing of 1, from m=−1 to m=1, is arranged in series order from l=1 to l=Lin. Furthermore, Sout is defined as vector of total Lout·(Lout+2) column in which each vector b at each integer timing of 1, from m=−1 to m=1, is arranged in series in order from l=1 to l=Lout. Yet further, Xin is defined as a vector of total Lin·(Lin+2) row obtained by transposing a vector in which each multipole moment α at each integer timing of 1, from m=−1 to m=1, is arranged in series order from l=1 to l=Lin. Yet further, Xout is defined as a vector of total Lout·(Lout+2) row obtained by transposing a vector in which each multipole moment β at each integer timing of 1, from m=−1 to m=1, is arranged in series order from l=1 to l=Lout.

$Sin = [a_{1,-1} a_{1,0} a_{1,+1} \cdots a_{Lin,Lin}]$ $Sout = [b_{1,-1} b_{1,0} b_{1,+1} \cdots b_{Lout,Lout}]$ $Xin = [\alpha_{1,-1} \alpha_{1,0} \alpha_{1,+1} \cdots \alpha_{Lin,Lin}]^t$ $Xout = [\beta_{1,-1} \beta_{1,0} \beta_{1,+1} \cdots \beta_{Lout,Lout}]^t$ [Expression 11]

Then, the sensor output vector Φ can be expressed in a form of an inner product of the matrix S and the column vector X as in the expression below. Herein, the matrix S represents the basis vector which is acquired by the signal space separating section 890 from the basis vector storage section 880 in step 1320, for example. Also, a column vector X represents a coefficient related to the basis vector.

$$\Phi = S \cdot X = [Sin, Sout] \cdot \begin{bmatrix} Xin \\ Xout \end{bmatrix}$$

Based on the model equation for the sensor output vector Φ obtained in Expression 12, the following equation is used to determine the column vector X that satisfies Φ=S·X in the least-squares approximation. This allows the signal space separating section 890 to solve for the spatial distribution of the magnetic field.

$$\hat{X} = \begin{bmatrix} \widehat{Xin} \\ \widehat{Xout} \end{bmatrix} = (S^t S) S^t \cdot \Phi$$

In this embodiment, as shown in FIG. 12, when calculating the magnetic field of the plurality of magnetic field positions 1200 on the surface of the living body 50, the magnetic field at the vector r of the plurality of magnetic field positions 1200 can be calculated based on the sensor output vector Φ by Expression 14 using X obtained by Expression 13. In Expression 14, the first term represents the magnetic field to be measured at the magnetic field position 1200 on the surface of the living body 50, and the second term represents the disturbance magnetic field.

$$B(r) = -\mu \sum_{l=1}^{Lin} \sum_{m=-l}^{l} \vec{X}_{in}(l,m) \cdot \nabla \left( \frac{1}{r^{l+1}} \cdot Y_{l,m}(\theta, \varphi) \right) - \quad \text{[Expression 14]}$$

$$\mu \sum_{l=1}^{Lout} \sum_{m=-l}^{l} \vec{X}_{out}(l,m) \cdot \nabla \left( r^l \cdot Y_{l,m}(\theta, \varphi) \right)$$

The signal space separating section 890 of this embodiment can calculate the magnetic field using Expression 14 for each of the plurality of magnetic field positions 1200 (1) to (M). The signal space separating section 890 outputs the result of suppressing the disturbance magnetic field component (that is, the component of the second term in Expression 14). The signal space separating section 890 may output only the magnetic field to be measured in vector r at magnetic field position 1200, that is, the component of the first term in Expression 14.

Next, in step 1350, the calculating section 895 calculates the current flowing in the living body 50 based on the magnetic field data B of the magnetic field component to be measured from the signal space separating section 890. The calculating section 895 may obtain the N currents J1 to JN shown in FIG. 12 from the M magnetic field data B1 to BM from the signal space separating section 890. First, the forward problem of converting current to magnetic field can be expressed as Expression 15 using the lead field matrix L. Herein, the magnetic fields B1 to BM and the currents J1 to JN are three-dimensional vectors, respectively. The values of the matrix elements of the lead field matrix L may be calculated by the finite element method (FEM), which models the living body 50.

$$B = L \cdot J \begin{pmatrix} B1 \\ B2 \\ \vdots \\ BM \end{pmatrix} = \begin{bmatrix} L11 & L12 & \dots & L1N \\ L21 & L22 & \dots & L2N \\ \dots & \dots & \dots & \dots \\ LM1 & LM2 & \dots & LMN \end{bmatrix} \begin{pmatrix} J1 \\ J2 \\ \vdots \\ JN \end{pmatrix} \quad \text{[Expression 15]}$$

After calculating the lead field matrix in the forward problem, the calculating section 895 may calculate the N currents J1 to JN as the inverse problem. In the inverse problem, the calculating section 895 can calculate the currents J1 to JN using the formula shown in Expression 17, respectively, to minimize the squared error as shown in Expression 16.

$$\min_{J1,J2,\dots,J} |B - \hat{B}|^2 \quad \text{[Expression 16]}$$

$$\hat{J} = (L^t L) L^t \cdot \hat{B} \quad \text{[Expression 17]}$$

As described above, the calculating section 895 can calculate the current at a plurality of positions in the living body 50 and output the current distribution in the living body 50. Step 1310 may be performed repeatedly, and after the measurement data corresponding to all electrode pairs have been acquired, the acquisition of measurement data for each current pair may be repeated in the same manner. Steps 1330 to 1350 may be performed in parallel with step 1310, and the calculation results can be output in real time while applying current and measuring magnetic field. The measuring apparatus 10 of this embodiment can generate and display an image showing the impedance distribution in the living body 50 according to the current distribution of the calculation results, using some of the EIT techniques, for example, by the display of the information processing section 30.

The measuring apparatus 10 of this embodiment can accurately detect the magnetic field on the outer surface of the living body 50 by suppressing the disturbance magnetic field with the signal space separating section 890. The measuring apparatus 10 of this embodiment can calculate the magnetic field of a large number of positions on the outer surface of the living body 50 based on the magnetic field detection results of the magnetic sensor array 210, thus increasing the resolution.

Figure 14:
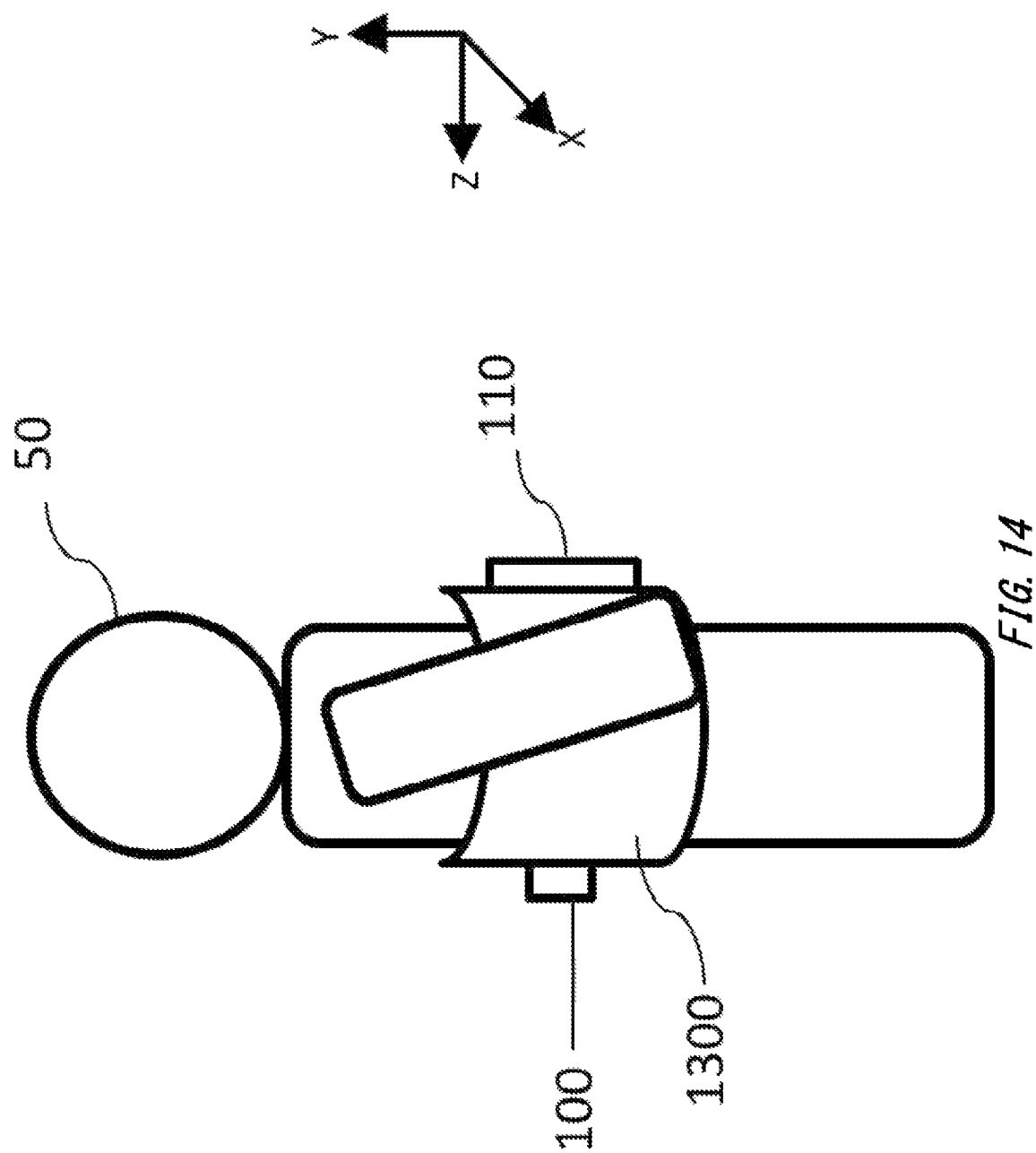
FIG. 14 illustrates a modification example of the measuring apparatus 10 according to the present embodiment.

FIG. 14 illustrates a part of a modification example of the measuring apparatus 10 according to the present embodiment. The measuring apparatus 10 in FIG. 14 has the same configuration as the measuring apparatus 10 in FIG. 1, except that the current applying section 100 and the magnetic sensor unit 110 are fixed in a belly-wrap configuration.

The measuring apparatus 10 of FIG. 14 has a fixing section 1300 for fixing at least one part of the current applying section 100 and at least one part of the magnetic sensor unit 110 to the living body 50. The fixing section 1300 may be cylindrical in shape with a changeable diameter of the hollow section, and the living body 50 may enter the hollow section and be fixed, thereby fixing the positional relationship between the living body 50 and at least one part of the current applying section 100 and at least one part of the magnetic sensor unit 110. As an example, the plurality of electrodes 800 of the current applying section 100 may be fixed to contact the living body 50 on one side of the fixing section 1300, and the magnetic sensor array 210 of the magnetic sensor unit 110 may be fixed to the other side of the fixing section 1300. The measuring apparatus 10 in FIG. 14 may not have to include the head 120, the driving section 125, the base section 130, and the pole section 140 shown in FIG. 1.

Note that in either embodiment, the magnetic sensor array 210 may or may not be in contact with the living body 50.

The measuring apparatus 10 may include at least one configuration in the main body 20 other than the electrodes 800 and the magnetic sensor array 210 in the information processing section 30.

Figure 15:
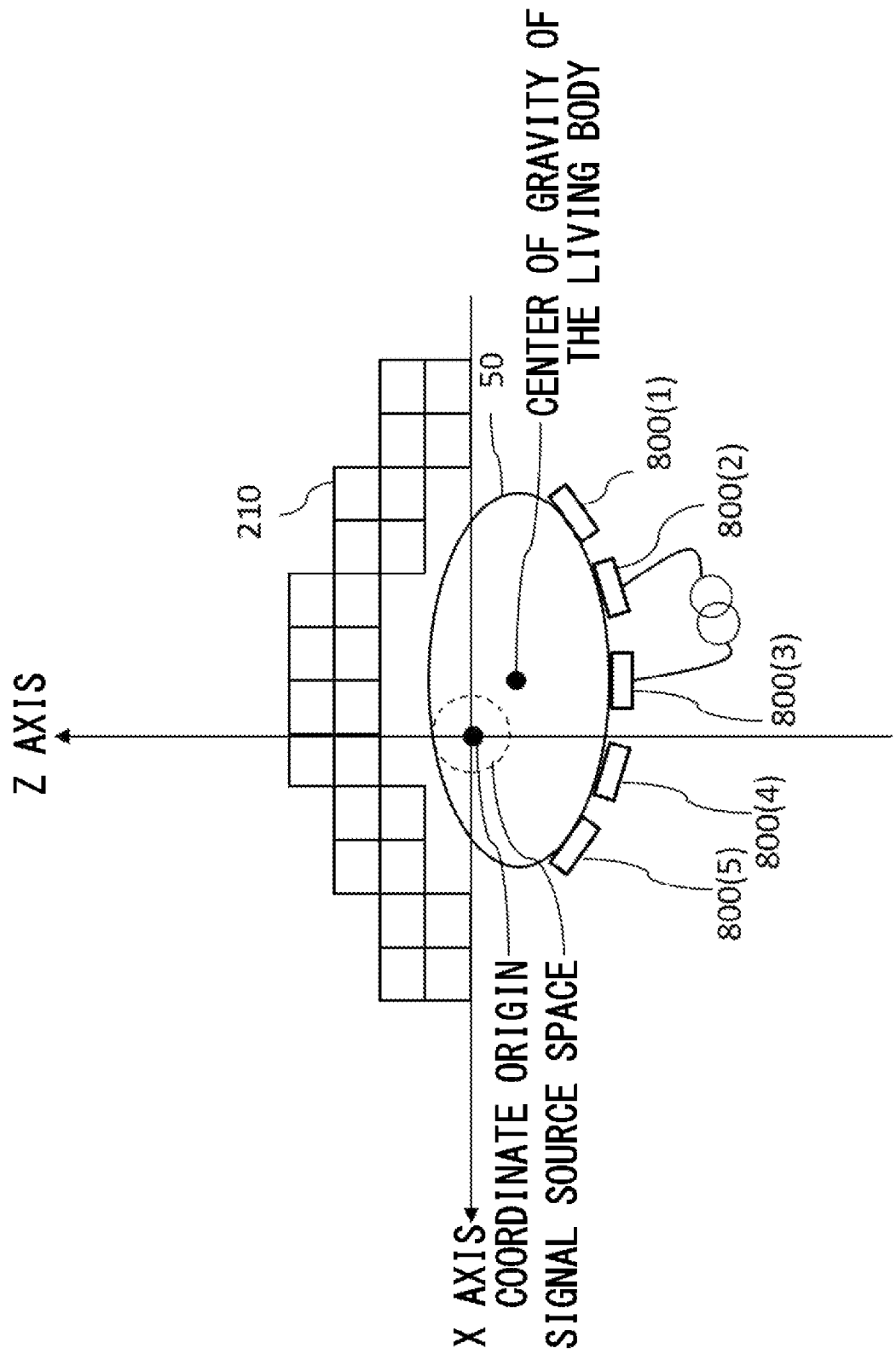
FIG. 15 illustrates an illustration for describing a modification example of a measuring method with the measuring apparatus 10 of the embodiment.
Figure 16:
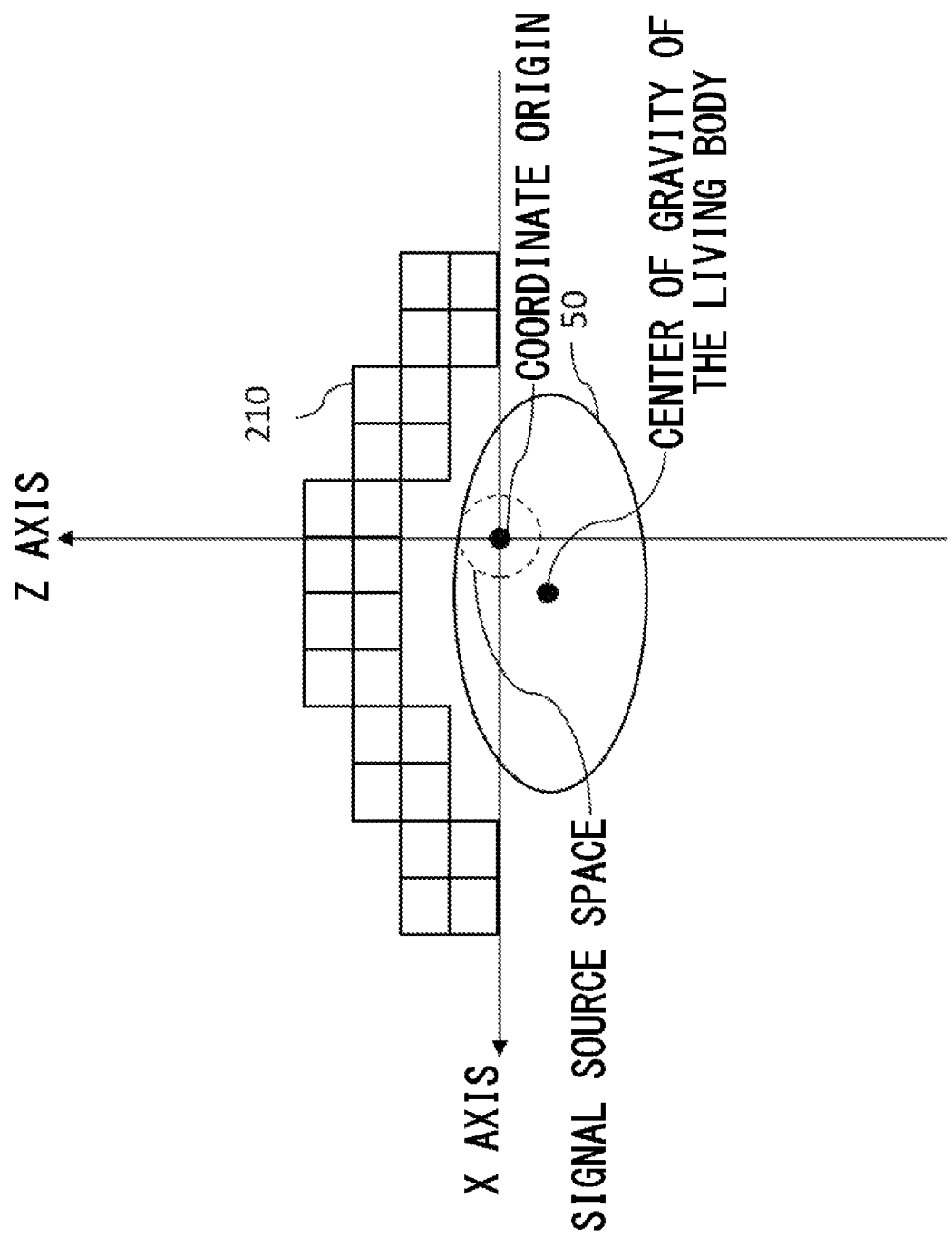
FIG. 16 illustrates an illustration for describing a modification example of the measuring method with the measuring apparatus 10 of the embodiment.

FIG. 15 and FIG. 16 are illustrations for describing a modification example of a measuring method with the measuring apparatus 10 of the embodiment. The measuring method of the modification example may have the same process as the measuring method described in FIG. 1 to FIG. 14 and may be performed by the measuring apparatus 10. However, in the measuring method described in FIG. 1 to FIG. 14, the signal space separating section 890 sets the position where the center of gravity of the living body 50 should be arranged as the coordinate origin, but in the measuring method of the modification example, the signal space separating section 890 sets a plurality of positions closer to the magnetic sensor array 210 than the position where the center of gravity of the living body 50 should be arranged as the respectively as the coordinate origin. In the following, the points that differ from the measuring method described in FIG. 1 to FIG. 14 are to be described.

In step 1300 of FIG. 13, the basis vector storage section 880 stores the magnetic field signal vector obtained by spatial sampling of the spherical harmonic function when the position closer to the magnetic sensor array 210 than the position where the center of gravity of the living body 50 should be arranged is specified as the coordinate origin as the basis vector. In FIG. 15, the coordinate origin is set to a position that is closer to the magnetic sensor array 210 than the position where the center of gravity of the living body 50 should be arranged, and is shifted to the positive direction (left side) in the X direction from that position. In FIG. 16, the coordinate origin is set to a position that is closer to the magnetic sensor array 210 than the position where the center of gravity of the living body 50 should be arranged, and is shifted to the negative direction (right side) in the X direction from that position. The coordinate origin in FIG. 15 and FIG. 16 may be set to a cross section parallel to the XZ plane, the same as the coordinate origin for the measuring methods described in FIG. 1 to FIG. 14. The basis vector storage section 880 may store the signal vectors on the left side of FIG. 15 and the signal vectors on the right side of FIG. 16 as basis vectors, respectively.

Herein, the center of gravity of the living body 50 may be, for example, the center of gravity of the cross section parallel to the XZ plane at the position where the electrodes are in contact with the living body 50, the center position of the maximum width in the X direction in that cross section, or the center position of the maximum width in the Z direction in that cross section.

In step 1320, the signal space separating section 890 obtains each of the signal vectors of the left and right sides stored as basis vectors by the basis vector storage section 880 in step 1300 from the basis vector storage section 880.

In step 1330, the signal space separating section 890 performs series expansion of the spatial distribution of the magnetic field indicated by the magnetic field measurement data B acquired in step 1310, using each of the signal vectors of the left and right sides acquired in step 1320 as the basis vector. The signal space separating section 890 then performs signal separation on each of the spatial distributions of the magnetic field on the right and left sides from the vector obtained by series expansion into the magnetic field to be measured and the disturbance magnetic field. In this way, the signal space separating section 890 may separate each of the spatial distributions of the plurality of different magnetic fields corresponding to the case where each of the plurality of positions closer to the magnetic sensor array 210 than the position where the center of gravity of the living body 50 should be arranged is set as the coordinate origin, into the magnetic field to be measured from the living body 50 and the disturbance magnetic field.

Then, in step 1340, the signal space separating section 890 calculates only each of the magnetic field to be measured on the right and left sides by suppressing the disturbance magnetic field based on the result of the signal separation in step 1330, and outputs it to the calculating section 895. The calculation of the magnetic fields to be measured on the right and left sides may be performed in the same way using Expression 6 to Expression 14, respectively.

Next, in step 1350, the calculating section 895 respectively calculates the current flowing in the living body 50 based on the magnetic field data B of the magnetic field components to be measured on the right and left sides from the signal space separating section 890. Thereby, the calculating section 895 of the estimation section 870 may calculate the current flowing through a plurality of different regions in the living body 50 (regions on the right and left sides in the living body 50) corresponding to the spatial distribution of the different plurality of magnetic fields, respectively.

In this embodiment, by making the coordinate origin closer to the magnetic sensor array 210, the signal source space where the signal source corresponding to the solution ^Xin of Expression 13 exists becomes narrower, thus reducing the degree of inappropriateness of the expression (for example, Expression 15 and so on) and enabling highly accurate detection of the current element contained in the signal source space. For example, by comparing the distribution of current flowing in regions on the right and left sides of the interior of the living body 50 (or two images showing the impedance distribution in the living body 50), abnormalities in these regions can be estimated. Therefore, the measuring method of the modification example is suitable for diagnosis of the lungs, such as pulmonary edema, as an example. In FIG. 15, the current is injected between two electrodes 800(2) and 800(3), so the magnetic field caused by the current flowing near these electrodes 800(2) and 800(3) and the current cables leading to these electrodes 800(2) and 800(3) in the living body 50 becomes the dominant component of the sensor vector signal D. However, in this embodiment, by making the coordinate origin closer to the magnetic sensor array 210, the signal source space can be narrowed, which makes it possible to increase the accuracy of the measurement for the signal source (current element) that is included in the signal source space and is the target to be measured.

Note that in the embodiment according to FIG. 1 to FIG. 16, each magnetic sensor cell 220 may not have to be capable of detecting magnetic fields in the three axial directions, and the magnetic sensor array 210 as a whole may be capable of detecting magnetic fields in the three axial directions.

Various embodiments of the present invention may be described with reference to flowcharts and block diagrams whose blocks may represent (1) steps of processes in which operations are performed or (2) sections of apparatuses responsible for performing operations. Certain steps and sections may be implemented by dedicated circuitry, programmable circuitry supplied with computer-readable instructions stored on computer-readable media, and/or processors supplied with computer-readable instructions stored on computer-readable media. Dedicated circuitry may include digital and/or analog hardware circuits and may include integrated circuits (IC) and/or discrete circuits. Programmable circuitry may include reconfigurable hardware circuits comprising logical AND, OR, XOR, NAND, NOR, and other logical operations, flip-flops, registers, memory elements, etc., such as field-programmable gate arrays (FPGA), programmable logic arrays (PLA), etc.

Computer-readable media may include any tangible device that can store instructions for execution by a suitable device, such that the computer-readable medium having instructions stored therein comprises an article of manufacture including instructions which can be executed to create means for performing operations specified in the flowcharts or block diagrams. Examples of the computer-readable medium may include an electronic storage medium, a magnetic storage medium, an optical storage medium, an electromagnetic storage medium, a semiconductor storage medium, and the like. More specific examples of the computer-readable medium may include a Floppy (registered trademark) disk, a diskette, a hard disk, a random access memory (RAM), a read-only memory (ROM), an erasable programmable read-only memory (EPROM or Flash memory), an electrically erasable programmable read-only memory (EEPROM), a static random access memory (SRAM), a compact disc read-only memory (CD-ROM), a digital versatile disk (DVD), a BLU-RAY (registered trademark) disc, a memory stick, an integrated circuit card, and the like.

Computer-readable instructions may include assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk (registered trademark), JAVA (registered trademark), C++, etc., and conventional procedural programming languages, such as the "C" programming language or similar programming languages.

Computer-readable instructions may be provided to a processor of a general purpose computer, special purpose computer, or other programmable data processing apparatus, or to a programmable circuitry, locally or via a local area network (LAN), wide area network (WAN) such as the Internet, or the like, to execute the computer-readable instructions to create means for performing operations specified in the flowcharts or block diagrams. Examples of the processor include a computer processor, a processing unit, a microprocessor, a digital signal processor, a controller, a microcontroller, and the like.

Figure 17:
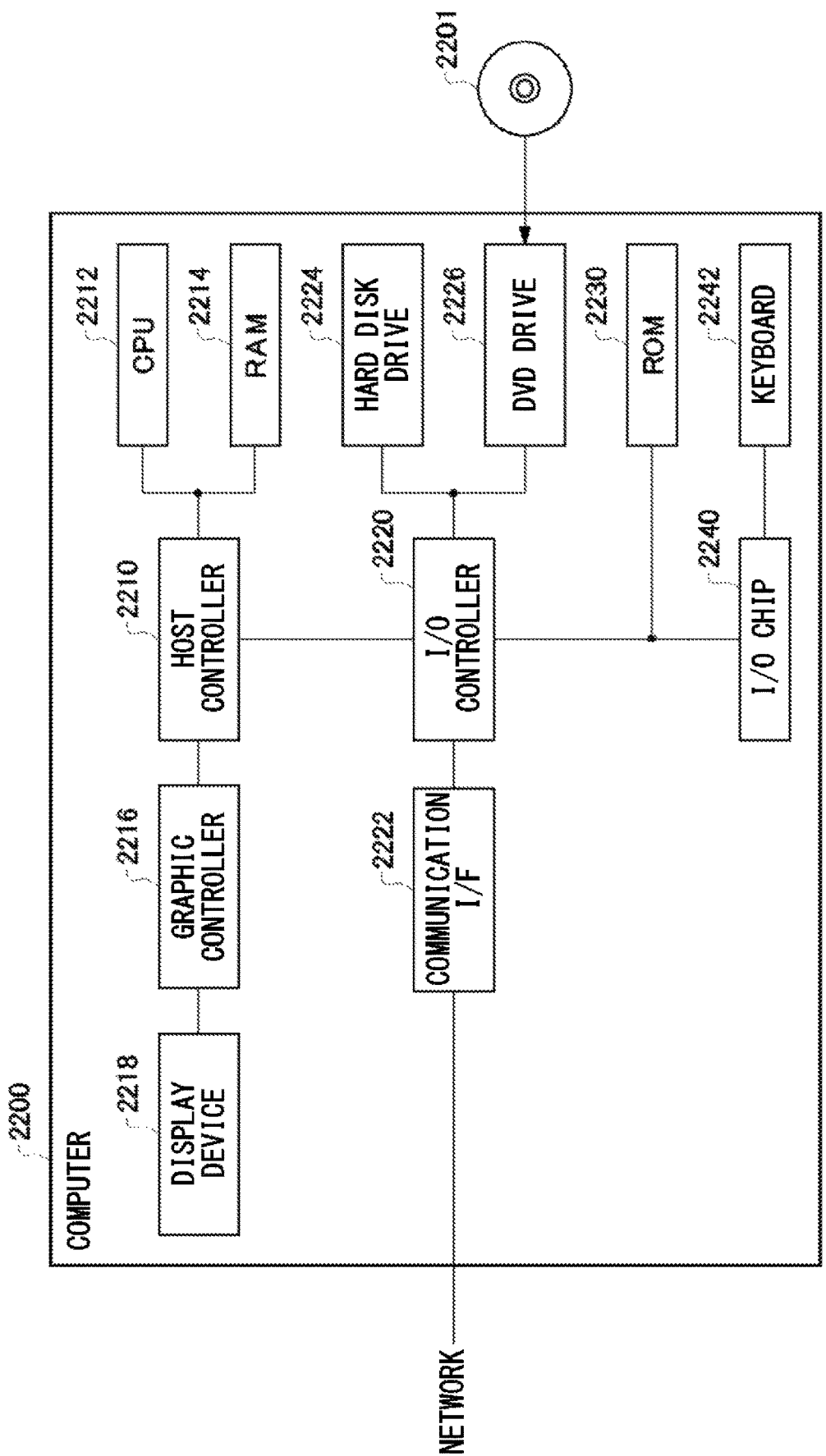
FIG. 17 illustrates an example of a computer 2200 in which a plurality of aspects of the present invention may be wholly or partly embodied.

FIG. 17 shows an example of a computer 2200 which multiple aspects of the present invention may be embodied entirely or partially. A program that is installed in the computer 2200 can cause the computer 2200 to function as or execute operations associated with the apparatus of the embodiment of the present invention or one or more sections thereof, and/or cause the computer 2200 to execute the process of the embodiment of the present invention or steps thereof. Such a program may be executed by the CPU 2212 to cause the computer 2200 to perform certain operations associated with some or all of the blocks of flowcharts and block diagrams described herein.

The computer 2200 according to the present embodiment includes a CPU 2212, a RAM 2214, a graphics controller 2216, and a display device 2218, which are interconnected by a host controller 2210. The computer 2200 also includes input/output units such as a communication interface 2222, a hard disk drive 2224, a DVD-ROM drive 2226, and an IC card drive, which are connected to the host controller 2210 via an input/output controller 2220. The computer also includes legacy input/output units such as a ROM 2230 and a keyboard 2242, which are connected to the input/output controller 2220 via an input/output chip 2240.

The CPU 2212 operates according to programs stored in the ROM 2230 and the RAM 2214, thereby controlling each unit. The graphics controller 2216 obtains image data generated by the CPU 2212 on a frame buffer or the like provided in the RAM 2214 or in itself, and causes the image data to be displayed on the display device 2218.

The communication interface 2222 communicates with other electronic devices via a network. The hard disk drive 2224 is configured to store programs and data used by the CPU 2212 within the computer 2200. The DVD-ROM drive 2226 is configured to read the programs or the data from the DVD-ROM 2201, and to provide the hard disk drive 2224 with the programs or the data via the RAM 2214. The IC card drive is configured to read programs and data from an IC card, and/or to write programs and data into the IC card.

The ROM 2230 is configured to store therein a boot program or the like that is executed by the computer 2200 at the time of activation, and/or a program depending on the hardware of the computer 2200. The input/output chip 2240 may also be configured to connect various input/output units to the input/output controller 2220 via a parallel port, a serial port, a keyboard port, a mouse port and the like.

A program is provided by a computer-readable medium such as the DVD-ROM 2201 or the IC card. The program is read from the computer-readable medium, is installed into the hard disk drive 2224, the RAM 2214 or the ROM 2230, which are also examples of the computer-readable medium, and is executed by the CPU 2212. The information processing described in these programs is read into the computer 2200, resulting in cooperation between a program and the above-mentioned various types of hardware resources. An apparatus or method may be constituted by realizing the operation or processing of information in accordance with the usage of the computer 2200.

For example, when a communication is executed between the computer 2200 and an external device, the CPU 2212 may execute a communication program loaded in the RAM 2214, and instruct the communication interface 2222 to process the communication based on the processing written in the communication program. The communication interface 2222, under control of the CPU 2212, reads transmission data stored on a transmission buffering region provided in a recording medium such as the RAM 2214, the hard disk drive 2224, the DVD-ROM 2201, or the IC card, and transmits the read transmission data to a network or writes reception data received from a network to a reception buffering region or the like provided on the recording medium.

In addition, the CPU 2212 may be configured to cause all or a necessary portion of a file or a database, which has been stored in an external recording medium such as the hard disk drive 2224, the DVD-ROM drive 2226 (DVD-ROM 2201) and the IC card, to be read into the RAM 2214, thereby executing various types of processing on the data on the RAM 2214. The CPU 2212 is configured to write back the processed data to the external recording medium.

Various types of information, such as various types of programs, data, tables, and databases, may be stored in the recording medium to undergo information processing. The CPU 2212 may also be configured to execute various types of processing on the data read from the RAM 2214, which includes various types of operations, processing of information, condition judging, conditional branching, unconditional branching, search/replacement of information and the like described in the present disclosure and designated by an instruction sequence of programs, and to write the result back to the RAM 2214. In addition, the CPU 2212 may search for information in a file, a database, etc., in the recording medium. For example, when a plurality of entries, each having an attribute value of a first attribute associated with an attribute value of a second attribute, are stored in the recording medium, the CPU 2212 may search for an entry matching the condition whose attribute value of the first attribute is designated, from among the plurality of entries, and read the attribute value of the second attribute stored in the entry, thereby obtaining the attribute value of the second attribute associated with the first attribute satisfying the predetermined condition.

The above-described program or software modules may be stored in the computer-readable medium on the computer 2200 or near the computer 2200. In addition, a recording medium such as a hard disk or a RAM provided in a server system connected to a dedicated communication network or the Internet can be used as the computer-readable medium, thereby providing the programs to the computer 2200 via the network.

While the embodiments of the present invention have been described, the technical scope of the invention is not limited to the above described embodiments. It is apparent to persons skilled in the art that various alterations and improvements can be added to the above-described embodiments. It is also apparent from the scope of the claims that the embodiments added with such alterations or improvements can be included in the technical scope of the invention.

The operations, procedures, steps, and stages of each process performed by an apparatus, system, program, and method shown in the claims, embodiments, or diagrams can be performed in any order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

EXPLANATION OF REFERENCES

10: measuring apparatus; 20: main body; 30: information processing section; 50: living bodies; 100: current applying section; 110: magnetic sensor unit; 120: head; 125: driving section; 130: base section; 140: pole section; 210: magnetic sensor array; 220: magnetic sensor cell; 230: sensor data gathering section; 300: sensor section; 520: magnetic sensor; 530: magnetic field generating section; 532: amplifier circuit; 534: coil; 540: output section; 702: magnetoresistive element; 704: magnetic flux concentrator; 706: magnetic flux concentrator; 800: electrode; 810: current applying section; 820: control section; 830: measurement data acquiring section; 840: AD converter; 842: clock generator; 850: calibration calculating section; 860: storage section; 870: estimation section; 880: basis vector storage section; 890: signal space separating section; 895: calculating section; 1200: magnetic field position; 1300: fixing section; 2200: computer; 2201: DVD-ROM; 2210: host controller; 2212: CPU: 2214: RAM; 2216: graphics controller; 2218: display device; 2220: input/output controller; 2222: communication interface; 2224: hard disk drive; 2226: DVD-ROM drive; 2230: ROM; 2240: input/output chip; 2242: keyboards

What is claimed is:

1. A measuring apparatus, comprising:
   an electrode unit including a plurality of electrodes in contact with a living body;
   a magnetic sensor array, including a plurality of magnetic sensor cells, capable of detecting input magnetic fields in three axial directions in a plurality of positions in a three-dimensional space;
   a current applying section configured to apply a current flowing in the living body by at least one electrode pair of the plurality of electrodes;
   a measurement data acquiring section configured to acquire measurement data based on the input magnetic field, which is detected from the living body by the magnetic sensor array during a current flows in the living body; and
   an estimation section configured to estimate a current flowing in the living body based on the measurement data;
   wherein the electrode unit and the magnetic sensor array are arranged opposite to one another and in a manner that allows at least a portion of the living body to be situated between the electrode unit and the magnetic sensor array during usage.

2. The measuring apparatus according to claim 1, wherein the current applying section is configured to apply an alternating current to flow in the living body by the at least one electrode pair.

3. The measuring apparatus according to claim 1, comprising a control section configured to synchronize the current flowing in the living body by the at least one electrode pair with an acquisition of the measurement data by the measurement data acquiring section.

4. The measuring apparatus according to claim 2, comprising a control section configured to synchronize the current flowing in the living body by the at least one electrode pair with an acquisition of the measurement data by the measurement data acquiring section.

5. The measuring apparatus according to claim 1, wherein the magnetic sensor array is arranged non-contact with the electrode unit.

6. The measuring apparatus according to claim 2, wherein the magnetic sensor array is arranged non-contact with the electrode unit.

7. The measuring apparatus according to claim 2, wherein the magnetic sensor array is arranged in a curved surface shape.

8. The measuring apparatus according to claim 1, wherein the plurality of electrodes are arranged to be arrayed in contact with the living body, and the current applying section is configured to apply a current to an electrode pair consisting of two electrodes of the plurality of electrodes to apply a current to flow in the living body.

9. The measuring apparatus according to claim 2, wherein the plurality of electrodes are arranged to be arrayed in contact with the living body, and the current applying section is configured to apply a current to an electrode pair consisting of two electrodes of the plurality of electrodes to apply a current to flow in the living body.

10. The measuring apparatus according to claim 8, wherein the current applying section is configured to apply a current to an electrode pair consisting of two adjacent electrodes in sequence while shifting the electrodes one by one to apply a current to flow in the living body.

11. The measuring apparatus according to claim 1, wherein
the estimation section comprises:
a signal space separating section configured to separate a spatial distribution of a magnetic field indicated by the measurement data into a magnetic field to be measured from the living body and a disturbance magnetic field; and
a calculating section configured to calculate a current flowing in the living body based on the magnetic field to be measured that has been separated.

12. The measuring apparatus according to claim 2, wherein
the estimation section comprises:
a signal space separating section configured to separate a spatial distribution of a magnetic field indicated by the measurement data into a magnetic field to be measured from the living body and a disturbance magnetic field; and
a calculating section configured to calculate a current flowing in the living body based on the magnetic field to be measured that has been separated.

13. The measuring apparatus according to claim 11, wherein
the plurality of magnetic sensor cells each includes a plurality of magnetic sensors having a magnetoresistive element and magnetic flux concentrators arranged on both ends of the magnetoresistive element; and
the signal space separating section is configured to separate a spatial distribution of the magnetic field with a signal vector, by using, as a basis vector, the signal vector, which is output by each of the plurality of magnetic sensors when the magnetic field with the spatial distribution of the orthonormal function is detected by the magnetic sensor array.

14. The measuring apparatus according to claim 11, wherein the signal space separating section is configured to separate a spatial distribution of the magnetic field when a position, closer to the magnetic sensor array than a position where a center of gravity of the living body is arranged, is set as a coordinate origin, into a magnetic field to be measured from the living body and a disturbance magnetic field.

15. The measuring apparatus according to claim 13, wherein the signal space separating section is configured to separate a spatial distribution of the magnetic field when a position, closer to the magnetic sensor array than a position where a center of gravity of the living body is arranged, is set as a coordinate origin, into a magnetic field to be measured from the living body and a disturbance magnetic field.

16. The measuring apparatus according to claim 14, wherein
the signal space separating section is configured to separate each of spatial distributions of the plurality of different magnetic fields into a magnetic field to be measured from the living body and a disturbance magnetic field, wherein the each of spatial distributions of the plurality of different magnetic fields being corresponded to a case where each of a plurality of positions, closer to the magnetic sensor array than a position where a center of gravity of the living body should be arranged, is set as a coordinate origin; and
the estimation section is configured to calculate a current flowing through a plurality of different regions in the living body corresponding to different spatial distributions of the plurality of magnetic fields, respectively.

17. The measuring apparatus according to claim 1, wherein the magnetic sensor array is arranged in a curved surface shape.

18. A non-transitory computer program product comprising a computer readable storage medium having program code embodied therewith, the program code executable by a computer to function as:
a signal space separating section configured to separate a spatial distribution of a magnetic field into a magnetic field to be measured from a living body and a disturbance magnetic field, wherein the spatial distribution of the magnetic field being indicated by measurement data based on an input magnetic field detected from the living body by a magnetic sensor array capable of detecting input magnetic fields in three axial directions in a plurality of positions in a three-dimensional space, while a current is being applied to flow in a living body by at least one electrode pair of a plurality of electrodes of an electrode unit in contact with the living body; and
a calculating section configured to calculate a current flowing in the living body based on the magnetic field to be measured that has been separated;
wherein the electrode unit and the magnetic sensor array are arranged opposite to one another and in a manner that allows at least a portion of the living body to be situated between the electrode unit and the magnetic sensor array during usage.

19. A measuring method, comprising:
applying a current to flow in a living body by at least one electrode pair of a plurality of electrodes of an electrode unit in contact with the living body;
acquiring, while a current is being applied to flow in the living body, measurement data based on an input magnetic field detected from the living body, by a magnetic sensor capable of detecting input magnetic fields in three axial directions in a plurality of positions in a three-dimensional space; and
estimating a current flowing in the living body based on the measurement data;
wherein the electrode unit and the magnetic sensor are arranged opposite to one another and in a manner that allows at least a portion of the living body to be situated between the electrode unit and the magnetic sensor array during usage.

* * * * *